(12) United States Patent
Martin et al.

(10) Patent No.: US 7,981,139 B2
(45) Date of Patent: Jul. 19, 2011

(54) SUTURE ANCHORS AND METHODS OF USE

(75) Inventors: Brian B. Martin, Boulder Creek, CA (US); Troy L. Thornton, San Francisco, CA (US)

(73) Assignee: Evalve, Inc, Redwood City, CA (US)

( * ) Notice: Subject to any disclaimer, the term of this patent is extended or adjusted under 35 U.S.C. 154(b) by 372 days.

(21) Appl. No.: 11/403,054

(22) Filed: Apr. 11, 2006

(65) Prior Publication Data

US 2006/0184203 A1    Aug. 17, 2006

Related U.S. Application Data

(63) Continuation of application No. 10/087,004, filed on Mar. 1, 2002, now Pat. No. 7,048,754.

(51) Int. Cl.
*A61B 17/04* (2006.01)
(52) U.S. Cl. ........................................ 606/232; 606/228
(58) Field of Classification Search .................. 606/108, 606/1, 53, 60, 76, 78, 99, 139–158, 222–233; 24/129 R, 129 B, 129 D
See application file for complete search history.

(56) References Cited

U.S. PATENT DOCUMENTS

| | | | |
|---|---|---|---|
| 2,097,018 A | 10/1937 | Chamberlain | |
| 2,108,206 A | 2/1938 | Meeker | |
| 3,296,668 A | 1/1967 | Aiken | |
| 3,378,010 A | 4/1968 | Codling et al. | |
| 3,671,979 A | 6/1972 | Moulopouslos | |
| 3,874,388 A | 4/1975 | King et al. | |
| 4,007,743 A | 2/1977 | Blake | |
| 4,056,854 A | 11/1977 | Boretos et al. | |
| 4,064,881 A | 12/1977 | Meredith | |
| 4,112,951 A | 9/1978 | Hulka et al. | |
| 4,235,238 A | 11/1980 | Ogiu et al. | |
| 4,297,749 A | 11/1981 | Davis et al. | |
| 4,425,908 A | 1/1984 | Simon | |
| 4,484,579 A | 11/1984 | Meno et al. | |

(Continued)

FOREIGN PATENT DOCUMENTS

DE    3504292    7/1986
(Continued)

OTHER PUBLICATIONS

Abe et al., De Vega's annuloplasty for acquired tricuspid disease: Early and late results in 110 patients, Ann. Thorac. Surg., 1989, 48:670-675.

(Continued)

*Primary Examiner* — (Jackie) Tan-Uyen T Ho
*Assistant Examiner* — Jing Rui Ou
(74) *Attorney, Agent, or Firm* — Sughrue Mion, PLLC; Jonathan Feuchtwang

(57) ABSTRACT

The present invention provides apparatuses, systems, methods and kits for fastening sutures or similar devices used in medical surgical procedures. In particular, the present invention is suitable for use with percutaneous or minimally invasive procedures in which sutures are placed with catheter-based devices wherein the tying of knots is particularly challenging. Suture fasteners of the present invention provide for fastening the sutures together in a fixed position at any location along the suture strands. In addition, the fasteners are adjustable to allow repositioning of the fastener after placement to a new desired location along the suture strands. Similarly, such fasteners may be used to hold a single suture strand for various applications.

9 Claims, 17 Drawing Sheets

U.S. PATENT DOCUMENTS

| | | |
|---|---|---|
| 4,487,205 A | 12/1984 | Di Giovanni et al. |
| 4,498,476 A | 2/1985 | Cerwin et al. |
| 4,510,934 A | 4/1985 | Batra |
| 4,578,061 A | 3/1986 | Lemelson |
| 4,686,965 A | 8/1987 | Bonnet et al. |
| 4,687,483 A | 8/1987 | Fisher et al. |
| 4,777,951 A | 10/1988 | Cribier et al. |
| 4,809,695 A | 3/1989 | Gwathmey et al. |
| 4,917,089 A | 4/1990 | Sideris |
| 4,944,295 A | 7/1990 | Gwathmey et al. |
| 4,969,890 A * | 11/1990 | Sugita et al. ............ 606/192 |
| 4,994,077 A | 2/1991 | Dobben |
| 5,015,249 A | 5/1991 | Nakao et al. |
| 5,019,096 A | 5/1991 | Fox, Jr. et al. |
| 5,042,707 A | 8/1991 | Taheri |
| 5,047,041 A | 9/1991 | Samuels |
| 5,049,153 A | 9/1991 | Nakao et al. |
| 5,061,277 A | 10/1991 | Carpentier et al. |
| 5,069,679 A | 12/1991 | Taheri |
| 5,108,368 A | 4/1992 | Hammerslag et al. |
| 5,125,758 A | 6/1992 | DeWan |
| 5,171,252 A | 12/1992 | Friedland |
| 5,171,259 A | 12/1992 | Inoue |
| 5,190,554 A | 3/1993 | Coddington et al. |
| 5,195,968 A | 3/1993 | Lundquist et al. |
| 5,209,756 A | 5/1993 | Seedhom et al. |
| 5,226,429 A | 7/1993 | Kuzmak |
| 5,251,611 A | 10/1993 | Zehel et al. |
| 5,254,130 A | 10/1993 | Poncet et al. |
| 5,282,845 A | 2/1994 | Bush et al. |
| 5,304,131 A | 4/1994 | Paskar |
| 5,306,283 A | 4/1994 | Conners |
| 5,306,286 A * | 4/1994 | Stack et al. ............ 623/1.12 |
| 5,312,415 A | 5/1994 | Palermo |
| 5,314,424 A | 5/1994 | Nicholas |
| 5,318,525 A | 6/1994 | West et al. |
| 5,320,632 A | 6/1994 | Heidmueller |
| 5,325,845 A | 7/1994 | Adair |
| 5,330,442 A | 7/1994 | Green et al. |
| 5,332,402 A | 7/1994 | Teitelbaum |
| 5,350,399 A | 9/1994 | Erlebacher et al. |
| 5,359,994 A | 11/1994 | Krauter et al. |
| 5,368,564 A | 11/1994 | Savage |
| 5,368,601 A | 11/1994 | Sauer et al. |
| 5,383,886 A | 1/1995 | Kensey et al. |
| 5,403,312 A | 4/1995 | Yates et al. |
| 5,403,326 A | 4/1995 | Harrison et al. |
| 5,411,552 A | 5/1995 | Andersen et al. |
| 5,417,699 A | 5/1995 | Klein et al. |
| 5,417,700 A | 5/1995 | Egan |
| 5,423,857 A | 6/1995 | Rosenman et al. |
| 5,423,858 A | 6/1995 | Bolanos et al. |
| 5,423,882 A | 6/1995 | Jackman et al. |
| 5,431,666 A | 7/1995 | Sauer et al. |
| 5,437,551 A | 8/1995 | Chalifoux |
| 5,437,681 A | 8/1995 | Meade et al. |
| 5,447,966 A | 9/1995 | Hermes et al. |
| 5,450,860 A | 9/1995 | O'Connor |
| 5,456,400 A | 10/1995 | Shichman et al. |
| 5,456,684 A | 10/1995 | Schmidt et al. |
| 5,462,527 A | 10/1995 | Stevens-Wright et al. |
| 5,472,044 A | 12/1995 | Hall et al. |
| 5,476,470 A | 12/1995 | Fitzgibbons, Jr. |
| 5,477,856 A | 12/1995 | Lundquist |
| 5,478,309 A | 12/1995 | Sweezer et al. |
| 5,478,353 A | 12/1995 | Yoon |
| 5,487,746 A | 1/1996 | Yu et al. |
| 5,489,297 A | 2/1996 | Duran |
| 5,507,725 A | 4/1996 | Savage et al. |
| 5,507,757 A | 4/1996 | Sauer et al. |
| 5,522,873 A | 6/1996 | Jackman et al. |
| 5,527,313 A | 6/1996 | Scott et al. |
| 5,527,321 A | 6/1996 | Hinchliffe |
| 5,527,322 A | 6/1996 | Klein et al. |
| 5,536,251 A | 7/1996 | Evard et al. |
| 5,540,705 A | 7/1996 | Meade et al. |
| 5,542,949 A | 8/1996 | Yoon |
| 5,554,185 A | 9/1996 | Block et al. |
| 5,569,274 A | 10/1996 | Rapacki et al. |
| 5,571,085 A | 11/1996 | Accisano, III |
| 5,571,137 A | 11/1996 | Marlow et al. |
| 5,571,215 A | 11/1996 | Sterman et al. |
| 5,575,802 A | 11/1996 | McQuilkin et al. |
| 5,582,611 A | 12/1996 | Tsuruta et al. |
| 5,593,424 A | 1/1997 | Northrup III |
| 5,593,435 A | 1/1997 | Carpentier et al. |
| 5,609,598 A | 3/1997 | Laufer et al. |
| 5,618,306 A | 4/1997 | Roth et al. |
| 5,620,452 A | 4/1997 | Yoon |
| 5,626,588 A | 5/1997 | Sauer et al. |
| 5,634,932 A | 6/1997 | Schmidt |
| 5,636,634 A | 6/1997 | Kordis et al. |
| 5,639,277 A | 6/1997 | Mariant et al. |
| 5,640,955 A | 6/1997 | Ockuly et al. |
| 5,649,937 A | 7/1997 | Bito et al. |
| 5,662,681 A | 9/1997 | Nash et al. |
| 5,669,917 A | 9/1997 | Sauer et al. |
| 5,695,504 A | 12/1997 | Gifford, III et al. |
| 5,695,505 A | 12/1997 | Yoon |
| 5,702,825 A | 12/1997 | Keital et al. |
| 5,706,824 A | 1/1998 | Whittier |
| 5,709,707 A | 1/1998 | Lock et al. |
| 5,713,910 A | 2/1998 | Gordon et al. |
| 5,713,911 A | 2/1998 | Racene et al. |
| 5,715,817 A | 2/1998 | Stevens-Wright et al. |
| 5,716,367 A | 2/1998 | Koike et al. |
| 5,718,725 A | 2/1998 | Sterman et al. |
| 5,722,421 A | 3/1998 | Francese et al. |
| 5,725,542 A | 3/1998 | Yoon |
| 5,725,556 A | 3/1998 | Moser et al. |
| 5,738,649 A | 4/1998 | Macoviak |
| 5,741,280 A | 4/1998 | Fleenor |
| 5,749,828 A | 5/1998 | Solomon et al. |
| 5,769,812 A | 6/1998 | Stevens et al. |
| 5,769,863 A | 6/1998 | Garrison |
| 5,772,578 A | 6/1998 | Heimberger et al. |
| 5,782,845 A | 7/1998 | Shewchuk |
| 5,797,927 A | 8/1998 | Yoon |
| 5,797,960 A | 8/1998 | Stevens et al. |
| 5,810,847 A | 9/1998 | Laufer et al. |
| 5,810,849 A | 9/1998 | Kontos |
| 5,810,853 A | 9/1998 | Yoon |
| 5,810,876 A | 9/1998 | Kelleher |
| 5,814,029 A | 9/1998 | Hassett |
| 5,820,592 A | 10/1998 | Hammerslag |
| 5,820,631 A | 10/1998 | Nobles |
| 5,823,955 A | 10/1998 | Kuck et al. |
| 5,823,956 A | 10/1998 | Roth et al. |
| 5,824,065 A | 10/1998 | Gross |
| 5,827,237 A | 10/1998 | Macoviak et al. |
| 5,829,447 A | 11/1998 | Stevens et al. |
| 5,833,671 A | 11/1998 | Macoviak et al. |
| 5,836,955 A | 11/1998 | Buelna et al. |
| 5,840,081 A | 11/1998 | Andersen et al. |
| 5,843,031 A | 12/1998 | Hermann et al. |
| 5,849,005 A | 12/1998 | Garrison et al. |
| 5,849,019 A | 12/1998 | Yoon |
| 5,853,422 A | 12/1998 | Huebsch et al. |
| 5,855,271 A | 1/1999 | Eubanks et al. |
| 5,855,614 A | 1/1999 | Stevens et al. |
| 5,860,990 A | 1/1999 | Nobles et al. |
| 5,868,733 A | 2/1999 | Ockuly et al. |
| 5,876,399 A | 3/1999 | Chia et al. |
| 5,879,307 A | 3/1999 | Chio et al. |
| 5,885,271 A | 3/1999 | Hamilton et al. |
| 5,891,160 A | 4/1999 | Williamson, IV et al. |
| 5,910,150 A | 6/1999 | Saadat |
| 5,916,147 A | 6/1999 | Boury |
| 5,928,224 A | 7/1999 | Laufer |
| 5,941,893 A | 8/1999 | Saadat |
| 5,944,733 A | 8/1999 | Engelson |
| 5,947,363 A | 9/1999 | Bolduc et al. |
| 5,954,732 A | 9/1999 | Hart et al. |
| 5,957,949 A | 9/1999 | Leonhard et al. |
| 5,972,020 A | 10/1999 | Carpentier et al. |
| 5,972,030 A | 10/1999 | Garrison et al. |
| 5,980,455 A | 11/1999 | Daniel et al. |

| | | | | | | |
|---|---|---|---|---|---|---|
| 5,989,284 | A | 11/1999 | Laufer | 6,641,592 | B1 | 11/2003 | Sauer et al. |
| 6,015,417 | A | 1/2000 | Reynolds, Jr. | 6,652,578 | B1 | 11/2003 | Bailey et al. |
| 6,019,722 | A | 2/2000 | Spence et al. | 6,669,687 | B1 | 12/2003 | Saadat |
| 6,022,360 | A | 2/2000 | Reimels et al. | 6,673,040 | B1 | 1/2004 | Samson et al. |
| 6,029,671 | A | 2/2000 | Stevens et al. | 6,685,648 | B2 | 2/2004 | Flaherty et al. |
| 6,033,378 | A | 3/2000 | Lundquist et al. | 6,695,866 | B1 | 2/2004 | Kuehn et al. |
| 6,036,699 | A | 3/2000 | Andreas et al. | 6,702,825 | B2 | 3/2004 | Frazier et al. |
| 6,048,351 | A | 4/2000 | Gordon et al. | 6,718,985 | B2 | 4/2004 | Hlavka et al. |
| 6,059,757 | A | 5/2000 | Macoviak et al. | 6,719,767 | B1 | 4/2004 | Kimblad |
| 6,060,628 | A | 5/2000 | Aoyama et al. | 6,730,016 | B1 | 5/2004 | Cox et al. |
| 6,060,629 | A | 5/2000 | Pham et al. | 6,743,239 | B1 | 6/2004 | Kueh et al. |
| 6,063,106 | A | 5/2000 | Gibson | 6,746,471 | B2 | 6/2004 | Mortier et al. |
| 6,066,146 | A | 5/2000 | Carroll et al. | 6,752,813 | B2 | 6/2004 | Goldfarb et al. |
| 6,068,628 | A | 5/2000 | Fanton et al. | 6,767,349 | B2 | 7/2004 | Ouchi |
| 6,068,629 | A | 5/2000 | Haissaguerre et al. | 6,769,434 | B2 | 8/2004 | Liddicoat et al. |
| 6,083,219 | A | 7/2000 | Laufer | 6,790,231 | B2 | 9/2004 | Liddicoat et al. |
| 6,086,600 | A | 7/2000 | Kortenbach | 6,797,002 | B2 | 9/2004 | Spence et al. |
| 6,088,889 | A | 7/2000 | Luther et al. | 6,860,179 | B2 | 3/2005 | Hopper et al. |
| 6,099,553 | A | 8/2000 | Hart et al. | 6,875,224 | B2 | 4/2005 | Grimes |
| 6,110,145 | A | 8/2000 | Macoviak | 6,896,690 | B1 | 5/2005 | Lambrecht et al. |
| 6,117,144 | A | 9/2000 | Nobles et al. | 6,902,522 | B1 | 6/2005 | Walsh et al. |
| 6,117,159 | A | 9/2000 | Huebsch et al. | 6,926,715 | B1 | 8/2005 | Hauck et al. |
| 6,123,699 | A | 9/2000 | Webster, Jr. | 6,942,694 | B2 | 9/2005 | Liddicoat et al. |
| 6,126,658 | A | 10/2000 | Baker | 6,945,978 | B1 | 9/2005 | Hyde |
| 6,132,447 | A | 10/2000 | Dorsey | 6,949,122 | B2 | 9/2005 | Adams et al. |
| 6,136,010 | A | 10/2000 | Modesitt et al. | 6,966,914 | B2 | 11/2005 | Abe |
| 6,159,240 | A | 12/2000 | Sparer et al. | 6,986,775 | B2 | 1/2006 | Morales et al. |
| 6,162,233 | A | 12/2000 | Williamson, IV et al. | 7,004,970 | B2 | 2/2006 | Cauthen, III et al. |
| 6,165,164 | A | 12/2000 | Hill et al. | 7,011,669 | B2 | 3/2006 | Kimblad |
| 6,165,183 | A | 12/2000 | Kuehn et al. | 7,018,408 | B2 | 3/2006 | Bailey et al. |
| 6,165,204 | A | 12/2000 | Levinson et al. | 7,048,754 | B2 | 5/2006 | Martin et al. |
| 6,168,614 | B1 | 1/2001 | Andersen et al. | 7,141,045 | B2 | 11/2006 | Johansson et al. |
| 6,171,320 | B1 | 1/2001 | Monassevitch | 7,186,262 | B2 | 3/2007 | Saadat |
| 6,182,664 | B1 | 2/2001 | Cosgrove | 7,192,442 | B2 | 3/2007 | Solem et al. |
| 6,187,003 | B1 | 2/2001 | Buysse et al. | 7,226,467 | B2 | 6/2007 | Lucatero et al. |
| 6,203,531 | B1 | 3/2001 | Ockuly et al. | 7,288,097 | B2 | 10/2007 | Séguin |
| 6,203,553 | B1 | 3/2001 | Robertson et al. | 7,381,210 | B2 | 6/2008 | Zarbatany et al. |
| 6,206,893 | B1 | 3/2001 | Klein et al. | 7,464,712 | B2 | 12/2008 | Oz et al. |
| 6,206,907 | B1 | 3/2001 | Marino et al. | 7,497,822 | B1 | 3/2009 | Kugler et al. |
| 6,210,419 | B1 | 4/2001 | Mayenberger et al. | 7,533,790 | B1 | 5/2009 | Knodel et al. |
| 6,210,432 | B1 | 4/2001 | Solem et al. | 7,559,936 | B2 | 7/2009 | Levine |
| 6,245,079 | B1 | 6/2001 | Nobles et al. | 7,563,267 | B2 | 7/2009 | Goldfarb et al. |
| 6,267,746 | B1 | 7/2001 | Bumbalough | 7,563,273 | B2 | 7/2009 | Goldfarb et al. |
| 6,267,781 | B1 | 7/2001 | Tu | 7,569,062 | B1 | 8/2009 | Kueh et al. |
| 6,269,819 | B1 | 8/2001 | Oz et al. | 7,604,646 | B2 | 10/2009 | Goldfarb et al. |
| 6,277,555 | B1 | 8/2001 | Duran et al. | 7,635,329 | B2 | 12/2009 | Goldfarb et al. |
| 6,283,127 | B1 | 9/2001 | Sterman et al. | 2001/0004715 | A1 | 6/2001 | Duran et al. |
| 6,283,962 | B1 | 9/2001 | Tu et al. | 2001/0005787 | A1 | 6/2001 | Oz et al. |
| 6,306,133 | B1 | 10/2001 | Tu et al. | 2001/0018611 | A1 | 8/2001 | Solem et al. |
| 6,309,382 | B1 | 10/2001 | Garrison et al. | 2001/0022872 | A1 | 9/2001 | Marui |
| 6,312,447 | B1 | 11/2001 | Grimes | 2001/0037084 | A1 | 11/2001 | Nardeo |
| 6,319,250 | B1 | 11/2001 | Falwell et al. | 2001/0039411 | A1 | 11/2001 | Johansson et al. |
| 6,322,559 | B1 | 11/2001 | Daulton et al. | 2001/0044568 | A1 | 11/2001 | Langberg et al. |
| 6,352,708 | B1 | 3/2002 | Duran et al. | 2002/0022848 | A1 | 2/2002 | Garrison et al. |
| 6,355,030 | B1 | 3/2002 | Aldrich et al. | 2002/0026233 | A1 | 2/2002 | Shaknovich |
| 6,358,277 | B1 | 3/2002 | Duran | 2002/0035381 | A1 | 3/2002 | Bardy et al. |
| 6,368,326 | B1 | 4/2002 | Dakin et al. | 2002/0042651 | A1 | 4/2002 | Liddicoat et al. |
| 6,379,345 | B1 | 4/2002 | Constantz | 2002/0055774 | A1 | 5/2002 | Liddicoat |
| 6,402,780 | B2 | 6/2002 | Williamson et al. | 2002/0055775 | A1 | 5/2002 | Carpentier et al. |
| 6,419,669 | B1 * | 7/2002 | Frazier et al. ............ 604/500 | 2002/0058995 | A1 | 5/2002 | Stevens |
| 6,461,366 | B1 | 10/2002 | Seguin | 2002/0077687 | A1 | 6/2002 | Ahn |
| 6,464,707 | B1 | 10/2002 | Bjerken | 2002/0087148 | A1 | 7/2002 | Brock et al. |
| 6,482,224 | B1 | 11/2002 | Michler et al. | 2002/0087169 | A1 | 7/2002 | Brock et al. |
| 6,485,489 | B2 | 11/2002 | Teirstein et al. | 2002/0087173 | A1 | 7/2002 | Alferness et al. |
| 6,491,511 | B1 | 12/2002 | Duran et al. | 2002/0103532 | A1 | 8/2002 | Langberg et al. |
| 6,508,828 | B1 | 1/2003 | Akerfeldt et al. | 2002/0107534 | A1 | 8/2002 | Schaefer et al. |
| 6,533,796 | B1 | 3/2003 | Sauer et al. | 2002/0147456 | A1 | 10/2002 | Diduch et al. |
| 6,540,755 | B2 | 4/2003 | Ockuly et al. | 2002/0158528 | A1 | 10/2002 | Tsuzaki et al. |
| 6,540,782 | B1 | 4/2003 | Snyders | 2002/0161378 | A1 | 10/2002 | Downing |
| 6,541,594 | B2 | 4/2003 | Ohrbom et al. | 2002/0183835 | A1 | 12/2002 | Taylor et al. |
| 6,551,331 | B2 | 4/2003 | Nobles et al. | 2003/0105519 | A1 | 6/2003 | Fasol et al. |
| 6,562,037 | B2 | 5/2003 | Paton et al. | 2003/0105520 | A1 | 6/2003 | Alferness et al. |
| 6,562,052 | B2 | 5/2003 | Nobles et al. | 2003/0120340 | A1 | 6/2003 | Lisk et al. |
| 6,575,971 | B2 | 6/2003 | Hauck et al. | 2003/0120341 | A1 | 6/2003 | Shennib et al. |
| 6,599,311 | B1 | 7/2003 | Biggs et al. | 2003/0130669 | A1 | 7/2003 | Damarati |
| 6,616,684 | B1 | 9/2003 | Vidlund et al. | 2003/0144697 | A1 | 7/2003 | Mathis et al. |
| 6,626,930 | B1 | 9/2003 | Allen et al. | 2003/0171776 | A1 | 9/2003 | Adams et al. |
| 6,629,534 | B1 | 10/2003 | Dell et al. | 2003/0187467 | A1 | 10/2003 | Schreck |
| 6,630,001 | B2 | 10/2003 | Duran et al. | 2003/0195562 | A1 | 10/2003 | Collier et al. |

| | | |
|---|---|---|
| 2003/0208231 A1 | 11/2003 | Williamson, IV et al. |
| 2003/0233038 A1 | 12/2003 | Hassett |
| 2004/0002719 A1 | 1/2004 | Oz et al. |
| 2004/0024414 A1 | 2/2004 | Downing |
| 2004/0044365 A1 | 3/2004 | Bachman |
| 2004/0049207 A1 | 3/2004 | Goldfarb et al. |
| 2004/0059351 A1 | 3/2004 | Eigler et al. |
| 2004/0078053 A1 | 4/2004 | Berg et al. |
| 2004/0092962 A1 | 5/2004 | Thorton et al. |
| 2004/0097878 A1 | 5/2004 | Anderson et al. |
| 2004/0111099 A1 | 6/2004 | Nguyen et al. |
| 2004/0111100 A1* | 6/2004 | Benderev et al. ............. 606/151 |
| 2004/0133082 A1 | 7/2004 | Abraham-Fuchs et al. |
| 2004/0133192 A1 | 7/2004 | Houser et al. |
| 2004/0152847 A1 | 8/2004 | Emri et al. |
| 2004/0186486 A1 | 9/2004 | Roue et al. |
| 2004/0186566 A1 | 9/2004 | Hindrichs et al. |
| 2004/0220593 A1 | 11/2004 | Greenhalgh |
| 2004/0236354 A1 | 11/2004 | Seguin |
| 2005/0004503 A1 | 1/2005 | Samson et al. |
| 2005/0004583 A1 | 1/2005 | Oz et al. |
| 2005/0004665 A1 | 1/2005 | Aklog |
| 2005/0021058 A1 | 1/2005 | Negro |
| 2005/0038508 A1 | 2/2005 | Gabbay |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0159810 A1 | 7/2005 | Filsoufi |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0267493 A1 | 12/2005 | Schreck et al. |
| 2005/0287493 A1 | 12/2005 | Novak et al. |
| 2006/0004247 A1 | 1/2006 | Kute et al. |
| 2006/0015003 A1 | 1/2006 | Moaddes et al. |
| 2006/0030866 A1 | 2/2006 | Schreck |
| 2006/0030867 A1 | 2/2006 | Zadno |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0089671 A1 | 4/2006 | Goldfarb et al. |
| 2006/0089711 A1 | 4/2006 | Dolan |
| 2006/0135993 A1 | 6/2006 | Seguin |
| 2006/0229708 A1 | 10/2006 | Powell et al. |
| 2007/0038293 A1 | 2/2007 | St.Goar et al. |
| 2007/0100356 A1 | 5/2007 | Lucatero et al. |
| 2007/0118155 A1 | 5/2007 | Goldfarb et al. |
| 2007/0129737 A1 | 6/2007 | Goldfarb et al. |
| 2007/0198082 A1 | 8/2007 | Kapadia et al. |
| 2008/0039935 A1 | 2/2008 | Buch et al. |
| 2008/0051703 A1 | 2/2008 | Thorton et al. |
| 2008/0051807 A1 | 2/2008 | St. Goar et al. |
| 2008/0097489 A1 | 4/2008 | Goldfarb et al. |
| 2008/0167714 A1 | 7/2008 | St. Goar et al. |
| 2008/0183194 A1 | 7/2008 | Goldfarb et al. |
| 2009/0156995 A1 | 6/2009 | Martin et al. |
| 2009/0163934 A1 | 6/2009 | Raschdorf, Jr. et al. |
| 2009/0177266 A1 | 7/2009 | Powell et al. |
| 2009/0198322 A1 | 8/2009 | Deem et al. |
| 2009/0270858 A1 | 10/2009 | Hauck et al. |
| 2009/0326567 A1 | 12/2009 | Goldfarb et al. |
| 2010/0016958 A1 | 1/2010 | St. Goar et al. |
| 2010/0022823 A1 | 1/2010 | Goldfarb et al. |

FOREIGN PATENT DOCUMENTS

| | | |
|---|---|---|
| EP | 0 179 562 | 7/1989 |
| EP | 0 684 012 A2 | 2/1995 |
| EP | 0 558 031 | 4/1999 |
| EP | 01674040 A2 | 6/2006 |
| GB | 1598111 | 9/1981 |
| GB | 2151142 | 7/1985 |
| JP | 11-089937 | 6/1999 |
| WO | WO 81/00668 | 3/1981 |
| WO | WO 91/01689 | 2/1991 |
| WO | WO 92/12690 | 8/1992 |
| WO | WO 94/18881 | 9/1994 |
| WO | WO 94/18893 | 9/1994 |
| WO | WO 96/22735 | 8/1996 |
| WO | WO 97/25927 | 7/1997 |
| WO | WO 97/39688 | 10/1997 |
| WO | WO 98/07375 | 2/1998 |
| WO | WO 98/30153 | 7/1998 |
| WO | WO 98/35638 | 8/1998 |
| WO | WO 99/00059 | 1/1999 |
| WO | WO 99/01377 | 1/1999 |
| WO | WO 99/07354 | 2/1999 |
| WO | WO 00/02489 | 1/2000 |
| WO | WO 00/03759 | 1/2000 |
| WO | WO 00/59382 A1 | 10/2000 |
| WO | WO 01/03651 A2 | 1/2001 |
| WO | WO 01/26557 | 4/2001 |
| WO | WO 01/26588 A2 | 4/2001 |
| WO | WO 01/28432 | 4/2001 |
| WO | WO 01/28455 | 4/2001 |
| WO | WO 01/66001 | 9/2001 |
| WO | WO 03/105667 A3 | 12/2003 |
| WO | WO 2004/082538 A2 | 3/2004 |
| WO | WO 2004/045378 A2 | 6/2004 |
| WO | WO 2004/082523 A2 | 9/2004 |
| WO | WO 2005/027797 A1 | 3/2005 |
| WO | WO 2005/032421 A2 | 4/2005 |
| WO | WO 2005/062931 A2 | 7/2005 |

OTHER PUBLICATIONS

Bailey, Surgery of the Heart, Chapter 20, 1995, pp. 686-737.

Maisano, The Edge to-edge technique: A simplified method to correct mitral insufficency, European Journal of Cardio-thoracic Surgery 13, 1998, pp. 240-246.

Reul et al., Mitral Valve Reconstruction for Mitral Insufficiency, Progress in Cardiovascular Diseases, No. 6, May/Jun. 1997, pp. 567-599, vol. XXXIX.

Supplementary Partial Search Report European Application No. 03743721, dated Feb. 3, 2009, 4 pages total.

Examination Report of European Application No. 03743721, dated Jun. 23, 2009, 5 pages total.

Agricola et al., "Mitral valve reserve in double orifice technique: an exercise echocardiographic study," Journal of Heart Valve Disease, (2002)11(5):637 643.

Alfieri et al., "Novel suture device for beating heart mitral leaflet approximation," Annals of Thoracic Surgery, (2002)74:1488 1493.

Alfieri et al., "The double orifice technique in mitral valve repair: a simple solution for complex problems," Journal of Thoracic Cardio-vascular Surgery, (2001)122:674 681.

Alfieri et al., "The edge to edge technique," The European Association for Cardio-Thoracic Surgry 14th Annual Meeting, (2000) Oct. 7-11, Book of Proceedings.

Alfieri , "The edge-to-edge repair of the mitral valve," [Abstract] 6th Annual NewEra Cardiac Care: Innovatiin & Technology, Heart Surgery Forum, (2003) pp. 103.

Alvarez et al., "Repairing the degenerative mitral valve: Ten- to fifteen-year follow-up" J. Thorac. Cardiovasc. Surg. (1996) 112:238-247.

Arisi et al., "Mitral valve repair with Alfieri technique in mitral regurgitation of diverse etiology: early echocardiographic results," Circulation Supplement II, (2001) 104(17):3240.

Bach et al., "Early improvement in congestive heart failure after correction of secondary mitral regurgitation in end-stage cardiomyopathy," Am. Heart J., (1995) 129:1165-1170.

Bach et al., "Improvement following correction of secondary mitral regurgitation in end-stage cardiomyopathy with mitral annuloplasty" Am. J. Cardiol., (1996) 78:966-969.

Bhudia, #58 Edge-to-edge mitral repair: a versatile mitral repair technique, 2003 STS Presentation, [Abstract Only].

Bhudia et al., "Edge-to-edge (Alfieri) mitral repair: results in diverse clinical settings," Ann Thorac Surg, 77: 1598-1606, (2004).

Bolling et al., "Surgery for acquired heart disease: Early outcome of mitral valve reconstruction in patients with end-stage cardiomyopathy ," Journal of Thoracic and Cardiovascular Surgery, (1995) 109:676-683.

Borghetti et al., "Preliminary observations on haemodynamics during physiological stress conditions following 'double-orifice' mitral valve repair," European Journal of Cardiothoracic Surgery, Apr. 18, (2001) 20:262-269.

Castedo, "Edge-to-edge tricuspid repair for redeveloped valve incompetence after DeVega's annuloplasty," AnnThora Surg, (2003) 75;605-6.

Dec et al., "Idiopathic dilated cardiomyopathy," N. Engl. J. Med., (1994) 331:1564-1575.

Dottori et al., "Echocardiographic imaging of the Alfieri type mitral valve repair," Ital Heart J, (2001) 2(4):319-320.

Downing et al., "Beating heart mitral valve surgery: Preliminary model and methodology," Journal of Thoracic and Cardiovascular Surgery, (2002) 123(6):1141-1146.

Falk et al., "Computer-enhanced mitral valve surgery: toward a total endoscopic procedure," Seminars in thoracic and cardiovascular surgery, (1999) 11(3):224-249.

Filsoufi et al., "Restoring Optimal Surface of Coaptation With a Mini Leaflet Prosthesis: A New Surgical Concept for the Correction of Mitral Valve Prolapse," Int'l. Soc. for Minimally Invasive Cardiothoracic Surgery 1(4):186-87 (2006).

Frazier et al., #62 Early Clinical Experience With an Implantable, Intracardiac Circulatory Support Device: Operative Considerations and Physiologic Implications, 2003 STS Presentation, 1 page total. [Abstract Only].

Fucci et al., "Improved results with mitral valve repair using new surgical techniques" Eur. J. Cardiothorac Sug. (1995) 9:621-627 (Medline Record enclosed herewith.).

Fundaro et al., "Chordal plication and free edge remodeling for mitral anterior leaflet prolapse repair: 8-year follow-up," Annals of Thoracic Surgery, (2001) 72:1515-1519.

Garcia-Rinaldi et al., "Left ventricular volume reduction and reconstruction is ischemic cardiomyopathy," Journal of Cardiac Surgery, (1999) 14:199-210.

Gateliene , "Early and postoperative results of metal and tricuspid valve insufficiency surgical treatment using edge-to-edge central coaptation procedure," (2002) 38 Suppl 2:172-5.

Gatti et al., "The edge to edge technique as a trick to rescue an imperfect mitral valve repair," Eur J Cardiothorac Surg, (2002) 22(5):817 20.

Gillinov et al., "Is minimally invasive heart valve surgery a paradigm for the future?," Current Cardiology Reports, (1999) 1:318-322.

Gundry, "Facile mitral valve repair utilizing leaflet edge approximation: midterm results of the Alfieri figure of eight repair," Presented at the Meeting of the Western Thoracic Surgical Association, (1999).

Gupta et al., #61 Influence of Older Donor Grafts on Heart Transplant Survival: Lack of Recipient Effects, 2003 STS Presentation, [Abstract Only].

Ikeda et al., "Batista's operation with coronary artery bypass grafting and mitral valve plasty for ischemic dilated cardiomyopathy," The Japanese Journal of Thoracic and Cardiovascular Surgery, (2000) 48:746-749.

Izzat et al., "Early experience with partial left ventriculectomy in the Asia-Pacific Region," Annuals of Thoracic Surgery, (1999) 67:1703-1707.

Källner et al., "Transaortic approach for the Alfieri Stitch," Ann Thorac Surg, 2001; 71:378-380.

Kameda et al., "Annuloplasty for severe mitral regurgitation due to dilated cardiomyopathy," Am. Thorac. Surg, (1996) 61:1829-1832.

Kavarna et al., "Transaortic repair of mitral regurgitation," Presented at the third annual New Era Cardiac Care conference, San Diego, CA, (2000) Jan. 13-16, http://www.hsforum.com/vol3/issue1/2000-2389print.html.

Kaza et al., "Ventricular reconstruction results in improved left ventricular function and amelioration of mitral insufficiency," Annals of Surgery, (2002) 235(6):828 832.

Khan et al., "Blade atrial septostomy: Experience with the first 50 procedures" Cathet. Cardiovasc. Diagn, (1991) 23:257-262.

Kherani et al., "Edge-to-edge mitral valve repair: the Columbia Presbyterian experience," Ann Thorac Surg, 2004; 78: 73-76.

Konertz et al., "Results after partial left ventriculectomy in a European heart failure population," J. Cardiac Surg, 1999; 14(2):129-135.

Kron et al., "Surgical relocation of the posterior papillary muscle in chronic ischemic mitral regurgitation," Annals. of Thoracic Surgery, (2002)74:600 601.

Krüger et al, "Edge to edge technique in complex mitral valve repair," Thorac Cardiovasc Surg, 2000, Thema: Poster, http://www.thieme.de/thoracic/abstracts/abstracts/p_73.html.

Langer et al., "Posterior mitral leaflet extensions: an adjunctive repair option for ischemic mitral regurgitation?," J. Thorac. Cardiovasc. Surf. 131:868-77 (2006).

Lorusso e al., "Double-Orifice technique to repair extensive mitral valve excision following acute endocarditis," J Card Surg, 1998; 13:24-26.

Lorusso et al., "The double-orifice technique for mitral valve construction: predictors of postoperative outcome," Eur J. Cardiothorac Surg, May 23, 2001; 20(3):583-589.

Maisano et al., "The double orifice repair for Barlow Disease: a simple solution for a complex repair," Supplement I Circulation, 1999; 100(18):1-94.

Maisano t al., "The double orifice technique as a standardized approach to treat mitral regurgitation due to severe myxomatous disease: surgical technique," Eur J. Cardiothoracic Surg., Jan. 18, 2000; 17:201-215.

Maisano, F. et al., "The hemodynamic effects of double-orifice valve repair for mitral regurgitation: a 3D computational model," European Journal of Cardio-thoracic Surgery, 1999; 15:419-425.

Maisano et al., "Valve repair for traumatic tricuspid regurgitation," Eur J. Cardio-Thorac Surg, 1996; 10:867-873.

Mantovani et al., "Edge-to-edge repair of congenital familiar tricuspid regurgitation: case report," J. Heart Valve Dis, Sep. 2000; 9 (5):641-643.

McCarthy et al. "Tricuspid valve repair with the Cosgrove-Edwards annuloplasty system" Am. Thorac. Surg., (1997) 64:267-268.

McCarthy et al., "Partial left ventriculectomy and mitral valve repair for end-stage congestive heart failure," Eur J. Cardio-thoracic Surgery, 1998; 13:337-343.

Moainie et al., Correction of traumatic tricuspid regurgitation using the double orifice technique, Annals of Thoracic Surgery, (2002) 73:963 965.

Morales et al., "Development of an off bypass mitral valve repair," The Heart Surgery Forum #1999-4963, (1999) 2(2):115-120.

Nakanishi et al., "Early outcome with the Alfieri mitral valve repair," J Cardiol, May 2001; 37(5):263-266, (Abstract in English; Article in Japanese.).

Nielsen et al., "The edge-to-edge mitral repair: tension on the approximating suture and leaflet deformation during acute ischemic mitral regurgitation in the ovine heart," Circulation, 2001;104 [ suppl 1]:I-29-I-35.

Noera et al.., "Tricuspid Valve Incompetence Caused by Nonpenetrating Thoracic Trauma", Annals of Thoracic Surgery, 1991, 51 (2), 320-322.

Osawa et al., "Partial left ventriculectomy in a 3 year old boy with dilated cardiomyopathy," Japanese Journal of Thoracic and Cardiovascular Surg, Sep. 2000, 48(9):590-593. [Abstract Only].

Park et al., "Clinical use of a blade atrial septostomy" Circulation (1978) 58:600-608.

Patel et al., #57 Epicardial Atrial Defibrillation: Novel Treatment of Postoperative Atrial Fibrillation, 2003 STS Presentation, [Abstract Only].

Privitera et al., "Mitral Valve Repair: Clinical Outcome and Pathology; Circulation," (2002) 106:173.

Redaelli et al., A computational study of the hemodynamics after 'edge-to-edge' mitral valve repair, Journal of Biomechanical Engineering, (2001) 123:565-570.

Ricchi et al., "Linear segmental annuloplasty for mitral valve repair" Ann. Thorac. Surg., (1997) 63:1805-1806.

Robicsek et al., #60 The Bicuspid Aortic Valve: How Does It Function? Why Does It Fail?, 2003 STS Presentation, [Abstract Only].

Tager et al., "Long-term follow-up of Rheumatic patients undergoing left-sided valve replacement with tricuspid annuloplasty—Validity of preoperative echocardiographic criteria in the decision to perform tricuspid annulopasty" Am. J. Cardiol., (1998) 81:1013-1016.

Tamura et al., Edge to edge repair for mitral regurgitation in a patient with chronic hemodialysis: report of a case, Kyobu Geka, (2001) 54(9):788-790. [Abstract Only].

Tibayan et al., #59 Annular Geometric Remodeling in Chronic Ischemic Mitral Regurgitation, 2003 STS Presentation, [Abstract Only].

Timek et al., "Edge-to-edge mitral repair: gradients and three-dimensional annular dynamics in vivo during inotropic stimulation," Eur J. of Cardiothoracic Surg., Jan. 9, 2001; 19:431-437.

Timek, "Edge-to-edge mitral valve repair without annuloplasty ring in acute ischemic mitral regurgitation," [Abstract] Clinical Science, Abstracts from Scientific Sessions, (2002) II-461.

Totaro et al., "Mitral valve repair for isolated prolapse of the anterior leaflet: an 11 year follow-up," Eur J. Cardio-Thoracic Surg, 1999; 15:119-126.

Uchida et al., "Percutaneous cardiomyotomy and valvultomy with angioscopic guidance," Am. Heart J., (1991) 121:1221-1224.

Umana et al., "'Bow-tie' mitral valve repair successfully addresses subvalvular dysfunction in ischemic mitral regurgitation," (1997) Surgical Forum pp. 279-280.

Umana, "'Bow-Tie' mitral valve repair: an adjuvant technique for ischemic mitral regurgitation," AnnThora Surg, (1998) 66:1640-6.

Votta et al., "3 D computational analysis of the stress distribution on the leaflets after edge to edge repair of mitral regurgitation," Journal of Heart Valve Disease, (2002)11:810 822.

* cited by examiner

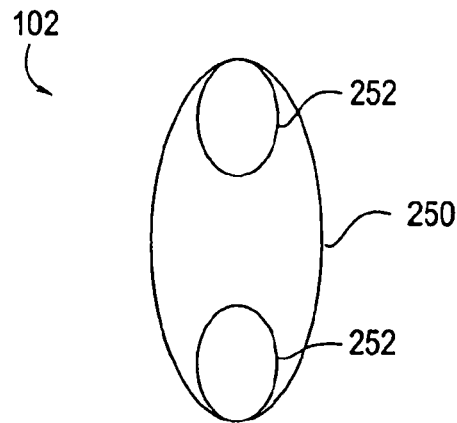
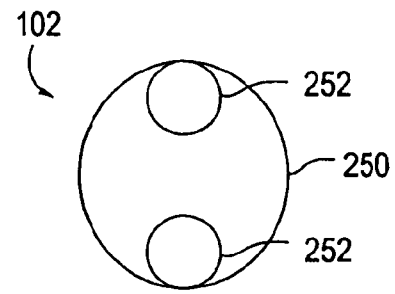
FIG. 7A  FIG. 7B
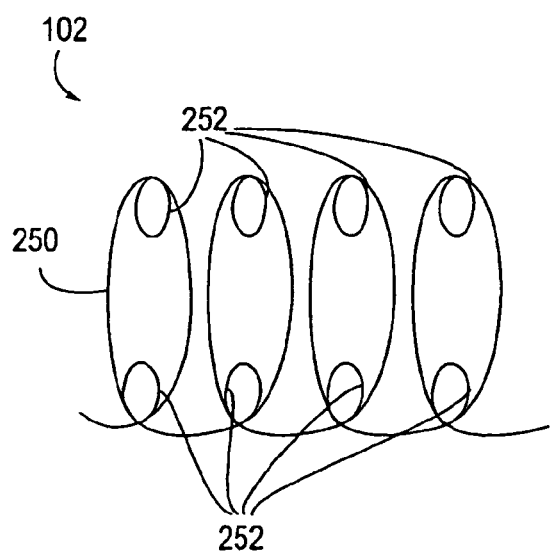
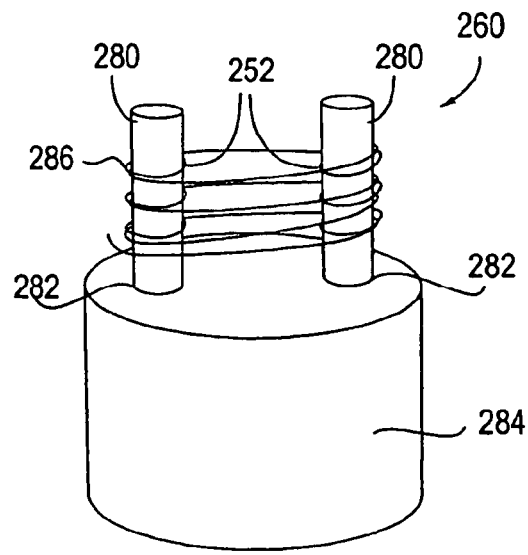
FIG. 8  FIG. 9

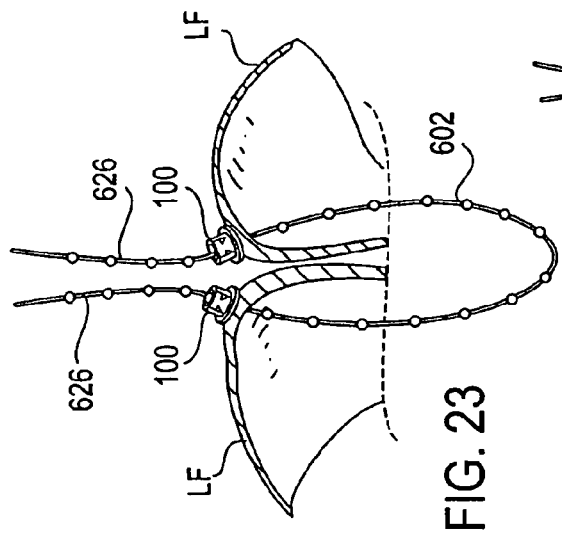
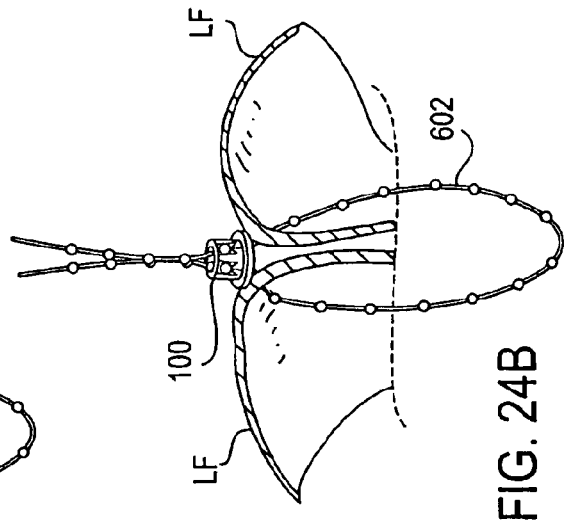
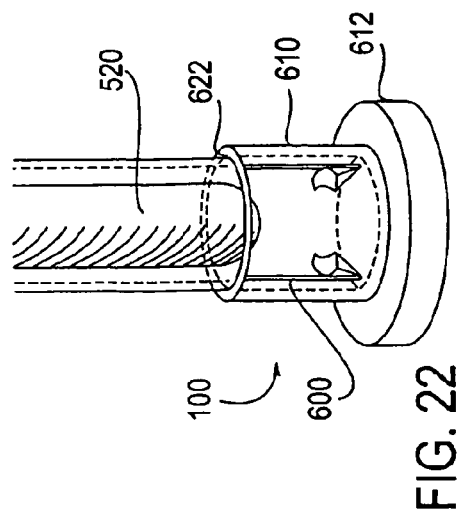
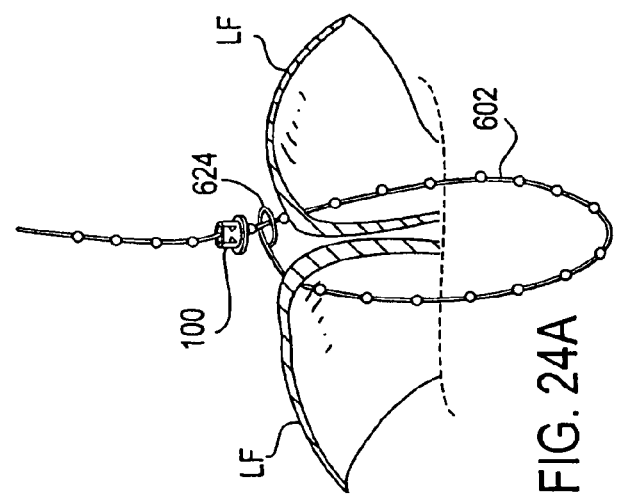

SUTURE ANCHORS AND METHODS OF USE

CROSS-REFERENCES TO RELATED APPLICATIONS

The present application is a continuation of U.S. patent application Ser. No. 10/087,004, filed Mar. 1, 2002, the full disclosure of which is incorporated herein by reference.

BACKGROUND OF THE INVENTION

1. Field of the Invention

The present invention relates generally to medical methods, systems and kits. Particularly, the present invention is related to methods and apparatuses for holding one or more suture strands in a configuration so as to fasten.

Sutures are typically used to hold tissue in desired positions, such as to close wounds or to correct malformations. The suture lines are threaded through the tissue any number of times and held in place to maintain the new tissue configuration. In order to hold the suture taught over an extended period of time, a knot is commonly formed in the suture ends. Suturing is often thought of as an art form learned over an extended period of time. There are many types of sutures and knots, each providing certain advantages in a particular operative setting. At least as complicated as the suturing itself is the knot-tying which must occur to secure each of the sutures. Where individual sutures are placed to close a long wound, an individual knot is tied in each place.

Knots differ considerably in their configuration, function, complexity and characteristics. By way of example, it will be noted that knots typically involve several throws of the sutures ends relative to each other. In one common knot, three half-hitches are used with the first half-hitch having four throws and each subsequent half-hitch having three throws. In this case, tying of a single knot to close a single suture involves ten throws. The simplest knots may be easier to tie, but in distant locations even the simple knots can be complicated where it is difficult to achieve proximity to the suture site. In these locations, more complicated slip knots have been used. These knots can be tied at a remote location and then slipped down to the surgical site. Except for a few extremely complex knots, slip knots have the undesirable tendency to slip in both directions. As a result, their ease of tying and movement to the surgical site is offset by their tendency to lose their grip at the suture site.

From these few examples, it can be appreciated that knots, as a suture-fastening system, are time-consuming, difficult to tie, hard to place, often unreliable as a holding system, difficult to adjust and impossible to relocate. This is particularly the case in the context of percutaneous, endovascular, laparoscopic, minimally invasive or robotic procedures. For these reasons, it would be desirable to provide alternative methods, systems, and kits for fastening sutures or similar devices which overcome at least some of the shortcomings noted above.

2. Description of the Background Art

Hart et al., U.S. Pat. No. 6,099,553, describes a suture system for closing a wound. The suture system includes a securing mechanism having a plurality of tines wherein the mechanism has a first position for capturing suture ends and a second position for permanently holding the suture ends in a fixed relationship. In a third position, the securing mechanism frictionally engages the suture ends in a sliding relationship.

Batra, U.S. Pat. No. 4,510,934, describes a surgical suture which consists of a monofilament core and a braided sheath surrounding the core. The core is later removed whereupon the sheath becomes flexible for tying into a secure knot.

BRIEF SUMMARY OF THE INVENTION

The present invention provides apparatuses, systems, methods and kits for fastening sutures or similar devices used in medical surgical procedures. In particular, the present invention is suitable for use with minimally invasive procedures in which sutures are placed with catheter-based devices wherein the tying of knots is particularly challenging. Suture fasteners of the present invention provide for fastening the sutures together in a fixed position at any location along the suture strands. In addition, the fasteners are adjustable to allow repositioning of the fastener after placement to a new desired location along the suture strands. Similarly, such fasteners may be used to hold a single suture strand for various applications.

In a first aspect of the present invention, the suture fastener for adjustably holding one or more suture strands comprises at least one fastening element comprised of a shape-recovery material or other suitable metal, polymer or combination, wherein the element has a tensioned position for engaging the suture strands while allowing sliding of the element relative to the suture strands and a relaxed shape-recovery position for holding the strands in a fixed position relative to the element or to each other. It may be appreciated that the term "tensioned position" is used to describe a position from which the element converts and assumes the shape-recovery position upon proper activation, such as stimulus or release or force. For example, the element may be placed under tension, compression, extension or any high potential energy state when in the tensioned position. Release of the force holding the element in this state allows the element to assume a relaxed shape-recovery position. Alternatively, the element may be in a tensioned position when no external force is applied but wherein the application of heat or energy transitions the form of the element to a relaxed shape-recovery position. Thus, the term "tensioned position" is not intended to limit the scope of the application to only positions under mechanical tension. In the tensioned position, the element holds the suture strands along a substantially straight path to provide ease of sliding. In the relaxed shape-recovery position, the element holds the suture strands along a tortuous path. In some embodiments, the suture strands are held along the same path and in others, wherein the suture strands comprise a first suture strand and a second suture strand, the first strand follows a first tortuous path and the second strand follows a second tortuous path which differs from the first tortuous path. And, in some embodiments, the tortuous path has a zig zag form or other non-linear form.

The suture fastener may take a variety of forms. In some embodiments, the suture fastener comprises a fastening element comprising a coil. In some of the coil embodiments, each turn of the coil has a circular, elliptical, square or triangular shape, to name a few, when the element has the relaxed shape-recovery position. In addition, the coil may further comprise at least one suture retention loop, typically having a circular or elliptical shape. The suture retention loop(s) of each coil turn may be disposed in diametrical opposition when the element has the relaxed shape-recovery position, such as along a long axis of the elliptical shape when so shaped. Alternatively, the suture retention loop(s) may be spaced along each coil turn in a uniform or varied pattern. In other embodiments, each turn of the coil has a figure-eight shape comprising two lobes when the element has the relaxed shape-recovery position and one suture retention loop is disposed within each lobe. The suture retention loops are thus disposed in concentric alignment when the element has the tensioned position.

In other embodiments, the suture fastener comprises a fastening element which has a flat shape when in the tensioned position and the element has a curved or bent shape in the relaxed shape-recovery position. For example, the element may comprise an elongate wire, ribbon, rod, filament or shaft having two or more apertures along its length. In preferred embodiments, the element comprises a ribbon having a width in the range of approximately 0.030 to 0.120 inches and a thickness in the range of approximately 0.002 to 0.020 inches. Suture strands are threaded through the apertures so that the element is slidable along the strands in the tensioned position. However, the curved shape of the element in the relaxed shape-recovery position prevents such sliding of the element and fixes the element in place.

In further embodiments, the suture fastener comprises two or more elements which interlock when the elements are in the relaxed shape-recovery position. Generally, the elements may be separated, straightened, held open or untwisted in the tensioned position so that the suture strands may be placed within or between them. In this arrangement, the elements may be moved relative to the suture strands to adjust the position of the elements along the strands. When the elements return to the relaxed shape-recovery position, the elements interlock around the strands so that the strands are held in a fixed position relative to the element and each other.

In additional embodiments, the suture fastener comprises a fastening element having a first edge having at least one first through hole adjacent thereto and a second edge having at least one second through hole adjacent thereto, wherein the at least one first aperture is concentrically aligned with the at least one second aperture when the element is in the tensioned position and the at least one first aperture is misaligned with the at least one second aperture when the element is in the relaxed shape-recovery position. The at least one pair of through holes may be bounded on all sides in both the tensioned position and the relaxed position. To achieve this, the element has a cylindrical or triangular shape wherein at least part of the first portion overlaps at least part of the second portion when the element is in the tensioned position. In this configuration, suture strands may be threaded through the apertures in a stitching-type fashion. Thus, transition of the element to the relaxed configuration draws the portions apart placing the strands along a tortuous path.

In any of the above embodiments, transition from the tensioned position to the relaxed position may be achieved by any means, such as by release of a force on the element or by a change in temperature of the element.

In a second aspect of the present invention, a method for securing two or more suture strands together comprises the steps of providing at least one fastening element comprised of a shape-recovery material, wherein the element is in a tensioned position for engaging the suture strands while allowing sliding of the element relative to the suture strands, engaging the suture strands with the element and transitioning the element to a relaxed shape-recovery position wherein the strands are in a fixed position relative to the element or to each other. The engaging step typically comprises positioning the suture strands along a path through at least a portion of the element. In some instances, the engaging step comprises positioning a first suture strand along a first path and a second suture strand along a second path which differs from the first path. When the element comprises a coil where each turn of the coil includes two suture retention loops, the positioning step may include positioning the suture strands through two or more suture retention loops. And when the suture retention loops of each coil turn are disposed in diametrical opposition when the element is in the relaxed shape-recovery position, the positioning step may include positioning the suture strands through successive suture retention loops so that the strands follow a path having a zig zag form when the element is in the relaxed shape-recovery position.

The providing step of the methods of the present invention may include loading the element on a loading tool. Alternatively, the element may already be loaded on the loading tool and the providing step comprises providing the element loaded on or within a loading tool. In either situation, the transitioning step comprises releasing the element from the loading tool.

When the element comprises an elongate wire, ribbon, rod, filament or shaft, the engaging step may comprise positioning the suture strands near at least two elements so that the elements capture the suture strands during the transitioning step by interlocking with each other. When the element comprises an elongate wire, ribbon, rod, filament or shaft having two or more apertures along its length, the positioning step may comprise positioning the suture strands through at least two apertures, such as in a stitching fashion. Similarly, when the element has a first portion having at least one first aperture and a second portion having at least one second aperture, the positioning step may comprise positioning the suture strands through at least one first aperture and at least one second aperture. This is easily achieved when the element has at least one first aperture concentrically aligned with at least one second aperture and the positioning step comprises positioning the suture strands through apertures in a stitching fashion.

With any of the above described embodiments of the fastening elements, the element may be slid along the suture strands to a desired position prior to transitioning to the relaxed shape-recovery position. Once transitioned, the position of the element along the suture strands may be adjusted. The adjusting step may comprise transitioning the element to the tensioned position and moving the element in relation to the suture strands.

In a third aspect of the present invention, a system for adjustably holding one or more suture strands comprises at least one fastening element comprised of a shape-recovery material, wherein the element has a tensioned position for engaging the suture strands while allowing sliding of the element relative to the suture strands and a relaxed shape-recovery position for holding the strands in a fixed position relative to the element or to each other, and a loading tool having a proximal end, a distal end and a lumen therethrough, wherein the element is loadable on the loading tool. In some embodiments, the loading tool further comprises a shaft near the distal end. In such instances, the element may comprise a coil which is mountable on the shaft. When each turn of the coil includes at least one suture retention loop, the coil may be loadable on the loading tool by inserting the shaft through at least one of the suture retention loops.

The system may further comprise at least one suture strand which is engageable by the element. Here, the loading tool may comprise a shaft near the distal end which houses at least a portion of the lumen through which the suture strand is threadable.

In a fourth aspect of the present invention, a suture fastening system for adjustably holding one or more suture strands comprises a delivery catheter comprising a proximal end, a distal end, and a lumen therethrough; and a suture fastener loadable on the distal end of the delivery catheter, said fastener comprising a ratcheting mechanism which is adapted to hold a suture strand at a first location and then release the strand and hold the strand at a second location upon adjustment, wherein the first and second locations are a predetermined distance apart. In some embodiments, the system further comprises at least one suture strand, wherein the strand has at least a first protuberance disposed near the first location and a second protuberance disposed near the second location. The suture strand may comprise a fiber, thread, filament, wire or cord and at least one protuberance may be selected from the group consisting of knots, beads, balls, ribs, and spokes. Further, the suture strand or at least one protuberance may be comprised of a material selected from the group consisting of stainless steel, nitinol, metal, polymer, silicone, latex, epoxy, cotton, nylon, polyester, and polytetrafluoroethylene-. In some embodiments, the ratcheting mechanism comprises at least two flexible arms having stoppers mounted thereon which are engageable with the protuberance. In most of these instances, the suture fastener may be loadable within the lumen of the delivery catheter.

In a fifth aspect of the present invention, a method for adjustably holding a suture strand comprises the steps of providing a delivery catheter comprising a proximal end, a distal end, and a lumen therethrough, loading a suture fastener on the distal end of the delivery catheter, said fastener comprising a ratcheting mechanism which is adapted to hold the suture strand at a first location and then hold the strand at a second location upon adjustment, wherein the first and second locations are a predetermined distance apart, and engaging the suture fastener with the suture strand at the first location. In some embodiments where the suture strand has at least a first protuberance disposed near the first location, wherein the ratcheting mechanism comprises at least two flexible arms each having a stopper mounted thereon which are engageable with the first protuberance, the loading step comprises positioning the suture strand so that the stopper engages the first protuberance. The method may further comprise adjusting the suture strand by advancing the strand through the fastener so that the fastener engages the strand at the second location. Thus, when the suture strand has at least a second protuberance disposed near the second location, wherein the ratcheting mechanism comprises at least two flexible arms each having a stopper mounted thereon which are engageable with the second protuberance, the loading step may comprise advancing the suture strand so that the stopper engages the second protuberance.

The methods, systems and apparatuses of the present invention may be provided in one or more kits for such use. The kits may comprise at least one fastening element comprised of a shape-recovery material, wherein the element has a tensioned position for engaging the suture strands while allowing sliding of the element relative to the suture strands and a relaxed shape-recovery position for holding the strands in a fixed position relative to the element or to each other, and instructions for use. Or, kits may comprise a ratcheting mechanism which is adapted to hold a suture strand at first location and then release the strand and hold the strand at a second location upon adjustment, wherein the first and second locations are a predetermined distance apart, and instructions for use. Optionally, such kits may further include any of the other system components described in relation to the present invention and any other materials or items relevant to the present invention.

It may be appreciated that in all embodiments of the methods of the present invention, the suture strand(s) held by the fastener may be cut at any distance from the fastener. In this way, the suture strands and fastener may be left in place as a temporary or permanent implant. Cutting of the sutures may be achieved by any suitable means. For instance, a cutting blade may be included in the delivery catheter which deploys the fastener. Or, a separate cutting catheter, tool, instrument or device may be used. Thus, such a cutting means may be included in any of the systems, apparatuses or kits of the present invention.

Other objects and advantages of the present invention will become apparent from the detailed description to follow, together with the accompanying drawings.

BRIEF DESCRIPTION OF THE DRAWINGS

FIGS. 7A-7B illustrate cross-sectional views of a fastening element having a coil shape.

FIG. 8 depicts a perspective view of a fastening element having a coil shape.

FIG. 9 illustrates a fixture for fabricating a fastening element having a coil shape.

FIG. 22 illustrates a housing having a flange wherein the ratchet of FIGS. 21A-21B is housed within.

FIG. 23 illustrates a pair of valve leaflets fixed together by a textured suture strand and ratcheted fasteners.

FIGS. 24A-24B illustrate a pair of valve leaflets fixed together by a textured suture strand and a single ratcheted fastener.

DETAILED DESCRIPTION OF THE INVENTION

Figure 1:
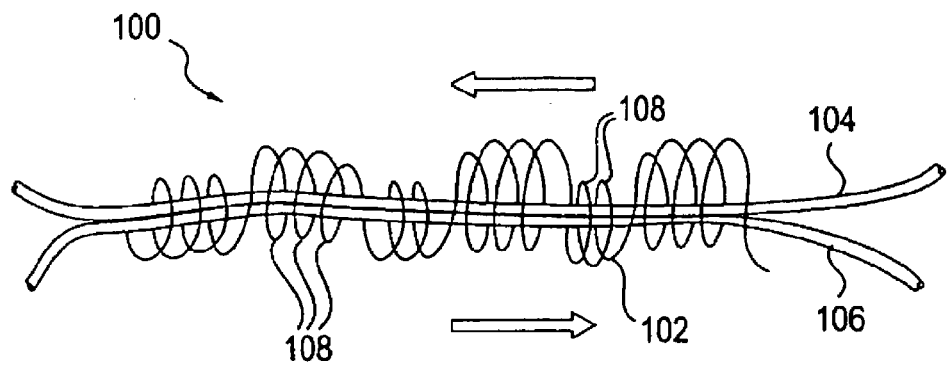
FIGS. 1-2 illustrate an embodiment of a suture fastener.
Figure 2:
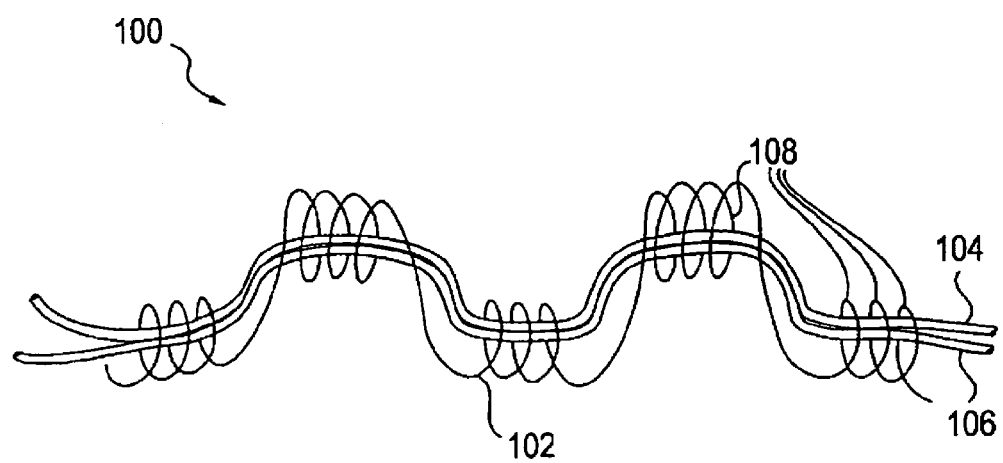

Referring to FIGS. 1-2, an embodiment of a suture fastener 100 is illustrated to provide an overview of the general features of the present invention. Here, the suture fastener 100 is comprised of a fastening element 102 having a coil shape. The element 102 is comprised of a shape-recovering material so that the element is able to return to a desired shape under certain conditions. For example, the shape-recovering material may be comprised of a shape-memory alloy, such as nitinol, or a spring-tempered steel. In this case, the element 102 may be placed in a tensioned position to form a first desired shape and release of the tension would allow the element 102 return to a relaxed shape-recovering position to form a second desired shape. These different shapes are useful in holding, adjusting and fastening one or more sutures.

For example, FIG. 1 illustrates a first suture strand 104 and a second suture strand 106 engaged by a fastening element 102. The element 102 has a coil shape wherein the suture strands 104, 106 are threaded through loops 108 of the coil while the element is maintained in a tensioned position. In this position, the loops 108 are generally aligned so that the suture strands 104, 106 are held along a substantially straight path. Thus, the element 102 may be slid back and forth, as indicated by arrows, relative to the suture strands 104, 106. Such sliding allows the element 102 to be advanced along the suture to a desired position for anchoring or fastening. Tension on the element 102 may then be released so that the element returns to a shape-recovering position. An example of such a position is shown in FIG. 2. Here, the element 102 holds the suture strands 104, 106 along a tortuous path having a zig zag form. In this position, the element 102 is not able to slide along the sutures as the tortuous path creates significant friction and resistance to sliding or slippage. Thus, the suture strands 104, 106 are fastened in place.

Figure 3:
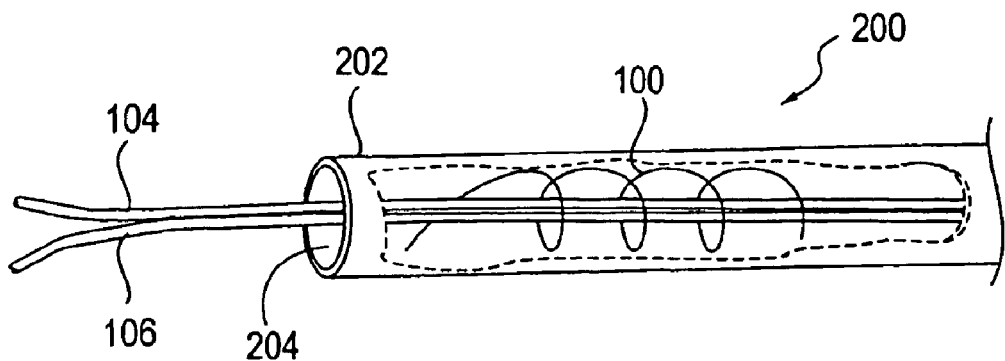
FIGS. 3-5 depict side views of a loading tool having a suture fastener loaded therein or thereon.
Figure 4:
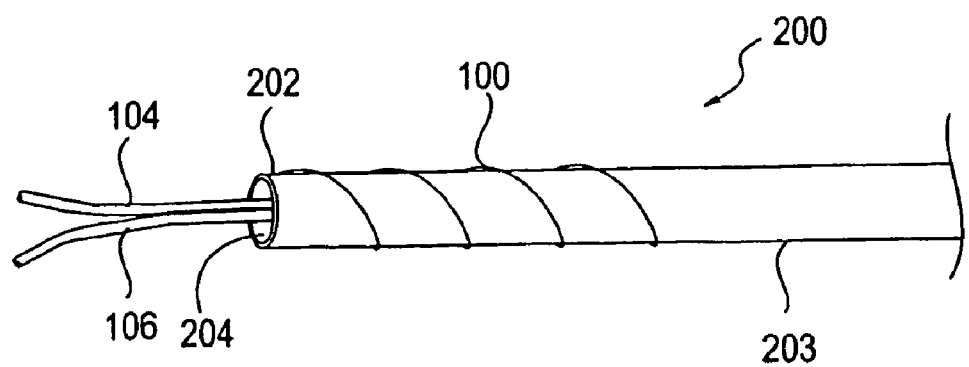
Figure 5:
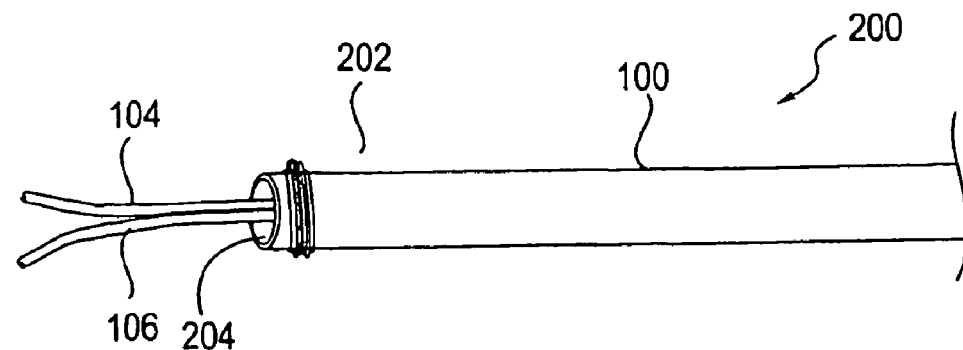

The suture fastener 100 may be introduced and deployed in a desired location with the use of a loading tool. In some embodiments, shown in FIGS. 3-5, the loading tool 200 has a proximal end (not shown), a distal end 202 and a lumen 204 therethrough. In each of these cases, suture strands 104, 106 are typically inserted through the lumen 204 as shown. Referring to FIG. 3, the fastener 100 may be loaded within the lumen 204 so that the suture strands 104, 106 are threaded through the fastener 100. The fastener 100 may then be deployed by pushing the fastener 100 out of the distal end 202 of the loading tool 200. Referring to FIG. 4, the fastener 100 may be loaded or mounted on the outside of the loading tool 200. Here, the fastener 100 is shown coiled around a shaft 203 of the loading tool 200 which houses the lumen 204 containing suture strands 104, 106. Thus, the fastener 100 may then be deployed by pushing the fastener 100 off the distal end 202 of the loading tool 200 so that the fastener 100 engages the suture strands 104, 106 at a desired location. Similarly, FIG. 5 illustrates a fastener 100 loaded on the outside of the loading tool 200. However, in this case the fastener 100 is shown coiled around the distal end 202 of the loading tool in a more compressed fashion. Such compression is desirable with some fastener 100 designs. Again, the fastener 100 may then be deployed by pushing the fastener 100 off the distal end 202 of the loading tool 200 so that the fastener 100 engages the suture strands 104, 106 at a desired location. It may be appreciated that the loading tool 200 may comprise a number of designs with the suture fastener 100 and/or suture strands 104, 106 having a number of arrangements for deployment and function of the suture fastener 100.

Figure 6C:
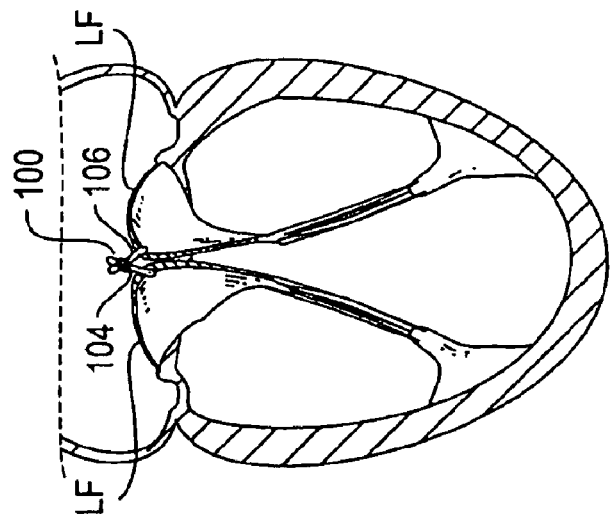
FIGS. 6A-6C illustrate usage of a suture fastener in fixing valve leaflets together.
Figure 6B:
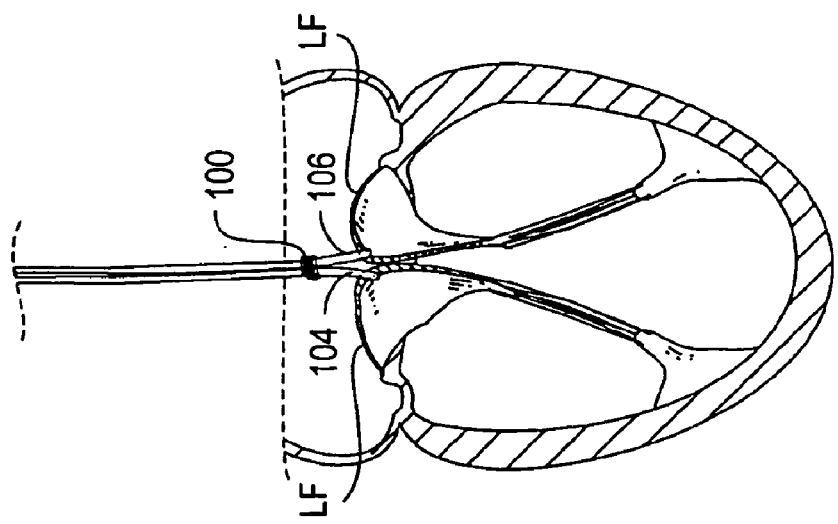
Figure 6A:
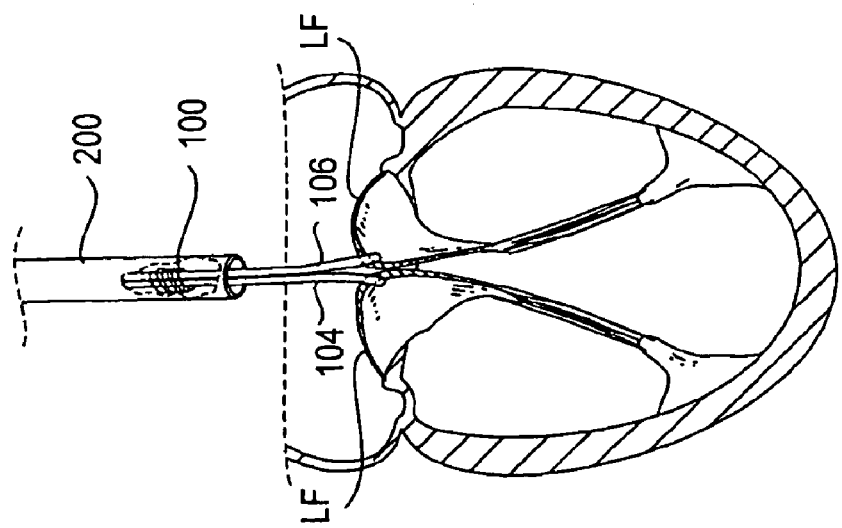

FIGS. 6A-6C illustrate a possible application for usage of the suture fastener 100. Here, valve leaflets LF are shown sutured together for treatment of valvular regurgitation. The first suture strand 104 and the second suture strand 106 are each attached to a valve leaflet LF by any suitable means. Rather than tying the suture strands 104, 106 together with a knot, a suture fastener 100 is used to fasten the strands 104, 106 together. In this example, the treatment procedure is performed with minimally invasive techniques wherein the valve leaflets are remotely accessed through the vascular system with the use of catheters. Thus, the loading tool 200 comprises a catheter which has been advanced through the vascular system to the leaflets LF. As shown in FIG. 6A, the loading tool 200, having the suture fastener 100 loaded within, approaches the site of the suture and the free ends of the suture strands 104, 106 are positioned within the lumen 204 of the loading tool 200. Referring now to FIG. 6B, the suture fastener 100 is then deployed at a desired location to hold the strands 104, 106 in a fixed position relative to the fastener 100 and/or to each other. The position of the fastener 100 may then be adjusted by sliding the fastener 100 along the suture strands 104, 106 to another desired location, such as closer to the leaflets LF as shown in FIG. 6C. Such adjustment is achieved by placing the fastener 100 in a tensioned position wherein the suture strands 104, 106 are engaged but not fixed, moving the fastener 100 along the strands 104, 106 and then returning the fastener 100 to a relaxed shape-recovery position to hold the strands 104, 106 in a fixed position. Once the fastener 100 has reached its final position, the strands 104, 106 may be cut and the fastener 100 left in place, as illustrated in FIG. 6C.

As mentioned, the suture fastener 100 is comprised of at least one fastening element 102 comprised of any type of shape-recovery material. This includes but is not limited to nitinol wire, spring-tempered steel, polymers, Elgiloy® (Elgin, Ill.) and the like. Likewise, the material may take any suitable form, such as round wire, flat wire, ribbon, hypotube, braid or cable. In many embodiments, the fastener 100 is comprised of 0.004-0.012 inch wire, preferably 0.008 inch superelastic nitinol wire. In some cases, the fastener 100 is heat-set by baking at approximately 450-560° C. for around 5-10 min, preferably approximately 7 min, followed by cool water quenching. The shape-recovery material allows the element 102 to have a tensioned position for engaging the suture strands while allowing sliding of the element relative to the suture strands and a relaxed shape-recovery position for holding the strands in a fixed position relative to the element or to each other. It may be appreciated that the element 102 is transitionable between the tensioned and relaxed position by application and release of force on the element 102, by a change in temperature of the element or by any other applicable means.

The fastening element 102 may take any number of forms suitable for holding suture strands along various paths, including substantially straight to various degrees of tortuous. In some embodiments, the element 102 comprises a coil 250. As shown in cross-section in FIGS. 7A-7B, each turn of the coil 250 may have, for example, an oval or elliptical shape, FIG. 7A, or a circular shape, FIG. 7B. In addition, each turn of the coil 250 may include at least one suture retention loop 252. Or, various turns of the coil 250 may include one or more suture retention loops 252 and other turns may include no suture retention loops. The suture retention loops 252 are often disposed in diametrical opposition when the element 102 is in the relaxed shape-recovery position. FIG. 8 provides a perspective view of the element 102 in the relaxed shape-recovery position, the element 102 having four turns of the coil 250, each turn having two diametrically opposed suture retention loops 252. During loading on or in the loading tool or at any other time when the element 102 is in the tensioned position, the suture retention loops 252 are disposed in concentric alignment. The element can undergo such deflection for loading on the loading tool with little or no permanent deformation due to the construction of the element 102, in particular the presence of the arched coil turn connecting the suture retention loops. Since the arches assume the deflection, the individual suture retention loops do not have as much strain placed on them and thus are able to more easily keep their shape. Concentric alignment of the loops 252 allows the suture strands 104, 106 to be advanced through the loops 252 along a substantially straight path for loading or repositioning of the element 102. Upon relaxation of the element 102, the strands are thus held along a tortuous path.

FIG. 9 illustrates a possible fixture 260 for fabricating the element 102. As shown, two 0.024 in stainless steel mandrels 280 are press fit into holes 282 in a base 284 and trimmed to about 1 cm extension. The shape-recovery wire 286 is then wrapped around the fixture 260 as shown. Since each loop 252 is made with the wire 286 starting on the outside of the mandrels 280 and then returning to the outside of the mandrels 280, the suture would be trapped on the inside of the loop 252 and cannot slip out. Consequently, each loop 252 can be made with only one wind to keep the suture contained.

Figure 10:
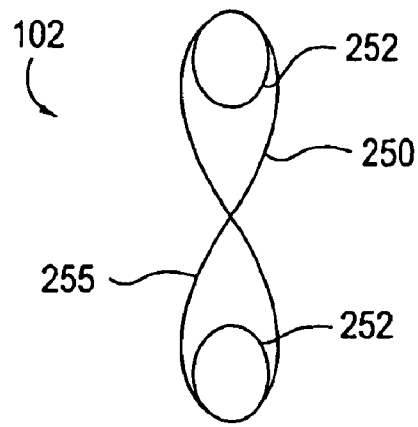
FIG. 10 illustrates a cross-sectional view of a fastening element having a FIG.-8 shape.
Figure 11:
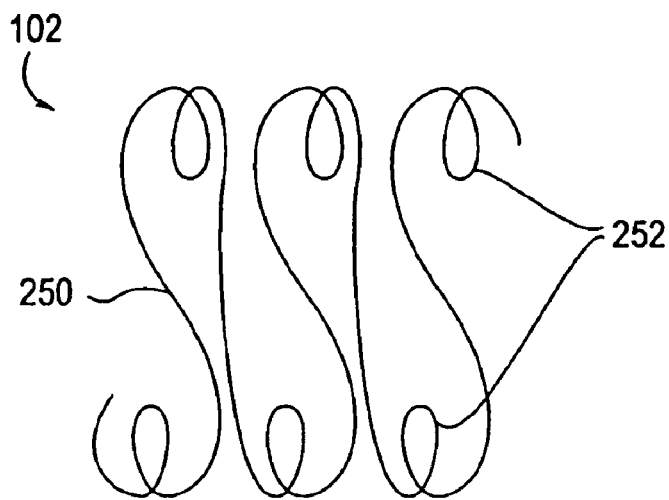
FIG. 11 depicts a perspective view of a fastening element having a FIG.-8 shape.
Figure 12:
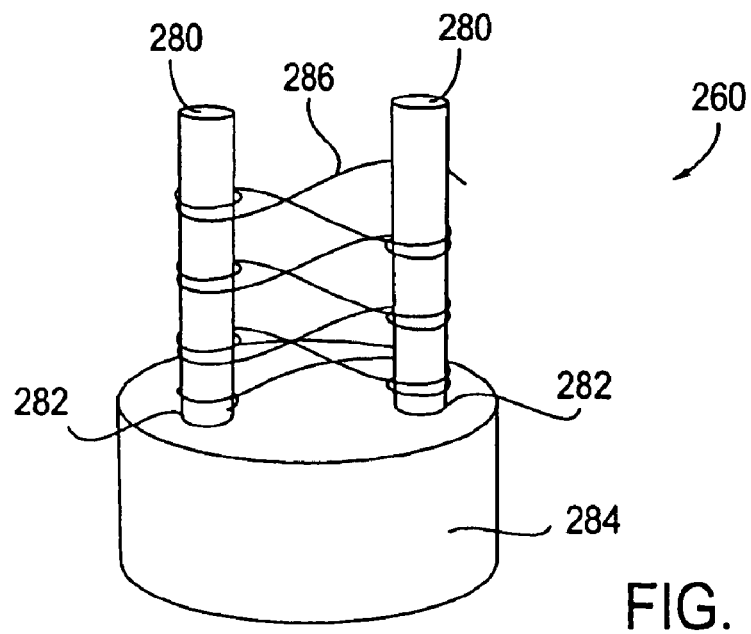
FIG. 12 illustrates a fixture for fabricating a fastening element having a FIG.-8 shape.

As shown in cross-section in FIG. 10, each turn of the coil 250 may have, for example, a FIG.-8 shape having two lobes 255. In addition, each turn of the coil 250 may include at least one suture retention loop 252 disposed within each lobe 255. Again, such loops 252 are typically disposed in diametrical opposition when the element 102 is in the relaxed shape-recovery position. FIG. 11 provides a perspective view of the element 102 in the relaxed shape-recovery position, the element 102 having four turns of the coil 250, each turn having two diametrically opposed suture retention loops 252. It may be appreciated that the suture retention loops 252 may be absent from some turns of the coil to allow for greater deflection or strain in the tensioned position. During loading on or in the loading tool or at any other time when the element 102 is in the tensioned position, the suture retention loops 252 are disposed in nearly concentric alignment. Such alignment of the loops 252 allows the suture strands 104, 106 to be advanced through the loops 252 along a substantially straight path for loading or repositioning of the element 102. Upon relaxation of the element 102, the strands are thus held along a tortuous path. FIG. 12 illustrates a possible fixture 280 for fabricating the element 102. As shown, two 0.024 in stainless steel mandrels 280 are press fit into holes 282 in a base 284 and trimmed to about 1 cm extension. The shape-recovery wire 286 is then wrapped around the fixture 260 as shown.

Figure 13:
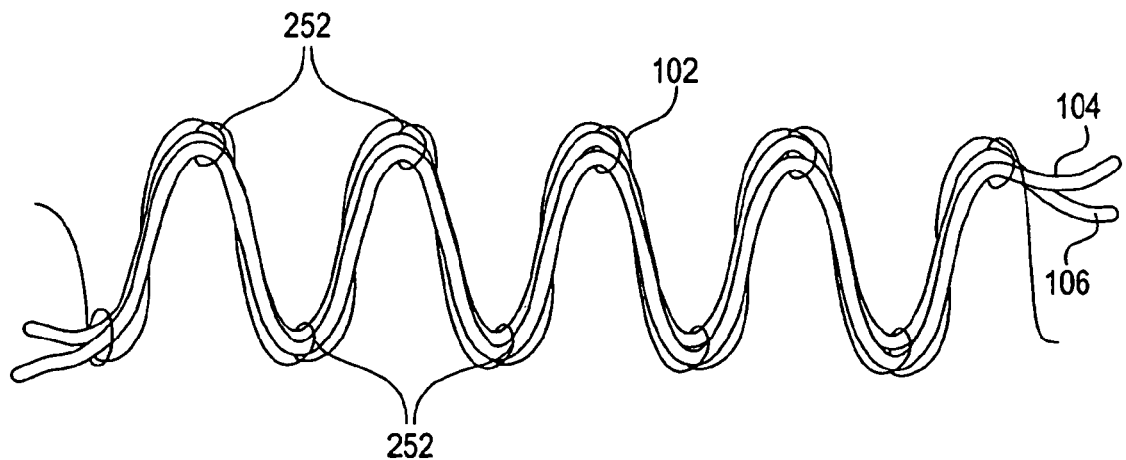
FIG. 13 illustrates suture strands held by a FIG.-8 shaped element in a relaxed shape-recovery position.
Figure 14:
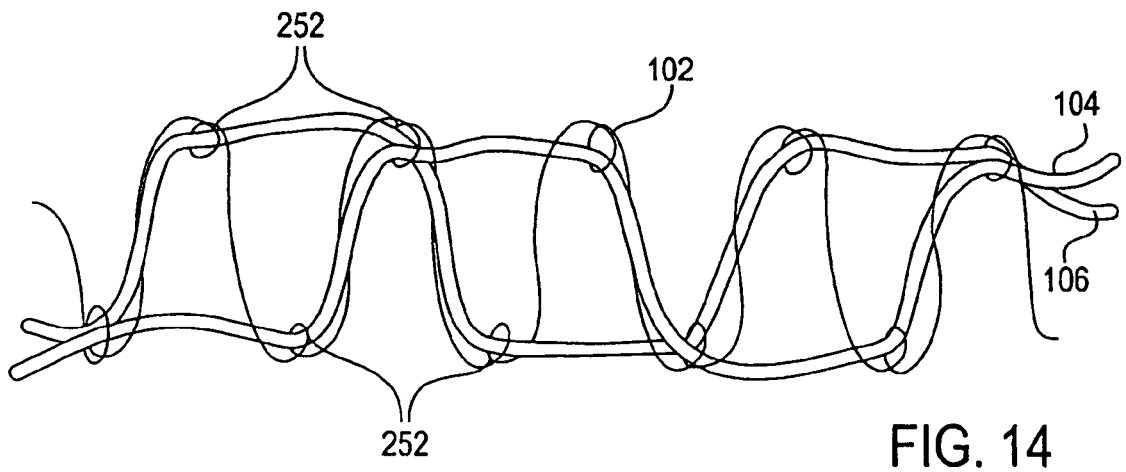
FIG. 14 illustrates suture strands held by a FIG.-8 shaped element in a relaxed shape-recovery position wherein each strand is held separately by the suture retention loops along separate paths.

FIGS. 13-14 illustrate suture strands 104, 106 held by the element 102 along tortuous paths in the relaxed shape-recovery position. Referring to FIG. 13, the element 102 has a FIG.-8 shape as described in relation to FIGS. 10-12. Here, the first suture strand 104 and the second suture strand 106 are shown held together by suture retention loops 252 in each turn of the coil 250. When the element 102 is in the relaxed shape-recovery position, as shown, the strands 104, 106 are held together along a tortuous zig zag path. Referring to FIG. 14, the element 102 again has a FIG.-8 shape but here the first suture strand 104 and the second suture strand 106 are held separately by suture retention loops 252. Thus, when the element 102 is in the relaxed shape-recovery position, the first strand 104 follows a first tortuous path and the second strand 106 follows a second tortuous path which differs from the first tortuous path.

Figure 26A:
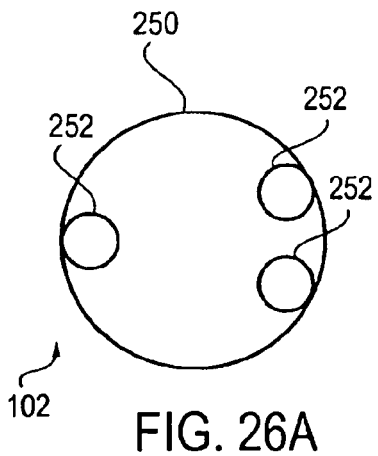
FIGS. 26A-26B, 27A-27B, 28A-28B illustrate additional embodiments of an element which holds suture strands, wherein each turn of the coil has various numbers and arrangements of suture retention loops.
Figure 26B:
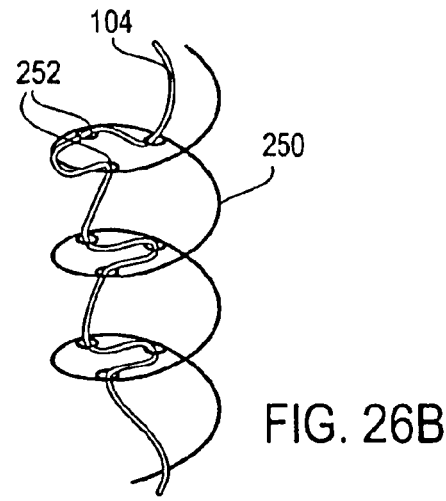
Figure 27A:
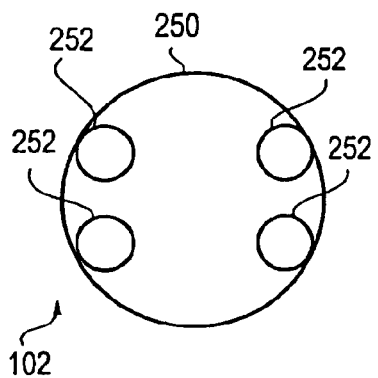
Figure 27B:
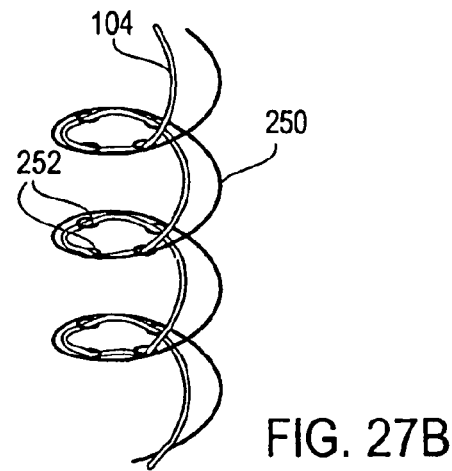
Figure 28A:
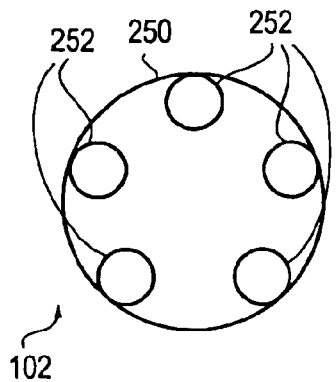
Figure 28B:
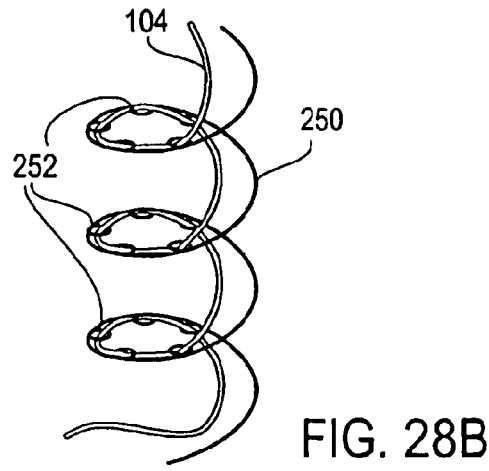
Figure 29:
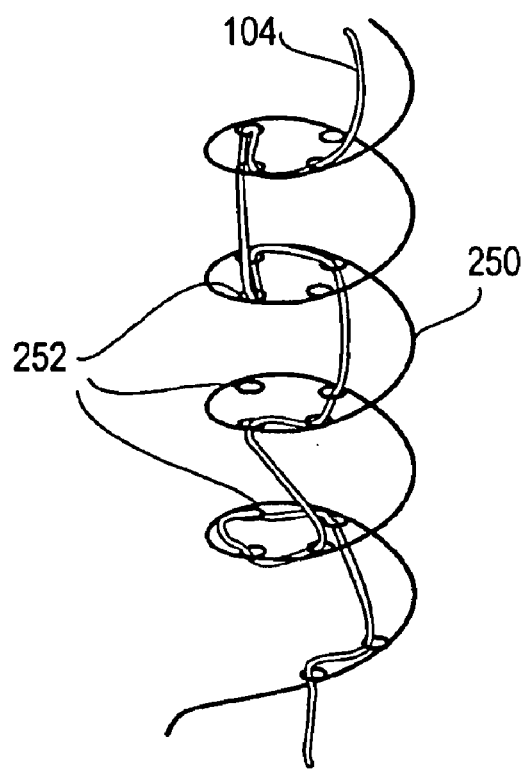
FIG. 29 illustrates an embodiment wherein a suture strand is threaded through the suture retention loops in a pattern that does not follow the shape of the coil.

FIGS. 26A-26B, 27A-27B, 28A-28B illustrate additional embodiments of the element 102 wherein each turn of the coil 250 has various numbers and arrangements of suture retention loops 252. In one embodiment shown in cross-section in FIG. 26A, each turn of the coil 250 has three suture retention loops 252. FIG. 26B provides a perspective view of the element 102 in the relaxed shape-recovery position, the element 102 having three turns of the coil 250, each turn having three suture retention loops 252. Also shown is a suture strand 104 threaded through the suture retention loops 252. In another embodiment shown in cross-section in FIG. 27A, each turn of the coil 250 has four suture retention loops 252. FIG. 27B provides a perspective view of the element 102 in the relaxed shape-recovery position, the element 102 having three turns of the coil 250, each turn having four suture retention loops 252. Also shown is a suture strand 104 threaded through the suture retention loops 252. And, in yet another embodiment shown in cross-section in FIG. 28A, each turn of the coil 250 has five suture retention loops 252. FIG. 28B provides a perspective view of the element 102 in the relaxed shape-recovery position, the element 102 having four turns of the coil 250, each turn having five suture retention loops 252. Again, also shown is a suture strand 104 threaded through the suture retention loops 252. Thus, generally, the more suture retention loops present, the more closely the threaded suture strand 104 follows the shape of the coil. However, as shown in FIG. 29, the suture strand 104 may be threaded through the loops 252 in a pattern that does not follow the shape of the coil 250, and additionally the suture strand 104 may not be threaded through all of the loops 252. It may be appreciated that each turn of the coil may have any number of retention loops and the suture retention loops 252 may be absent from some turns of the coil to allow for greater deflection or strain in the tensioned position.

Figure 30:
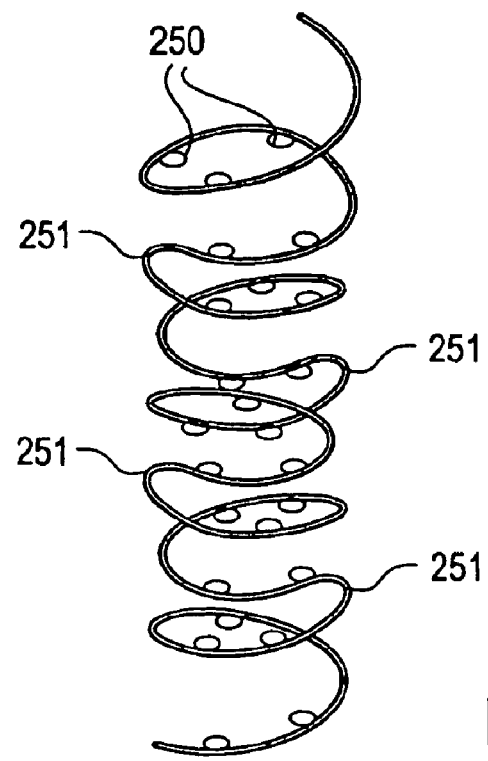
FIG. 30 illustrates an embodiment of an element wherein the coil is formed by alternating the direction of the wind.

FIG. 30 illustrates an embodiment of the element 102 wherein the coil 250 is formed by alternating the direction of the wind. As shown, the coil 250 reverses direction of the wind at reverse points 251. This provides a slightly different relaxed shape-recovery position from the standard coil shape and responds differently when in the tensioned position. As shown, the suture retention loops 252 may still be located within each turn of the coil.

Figure 31:
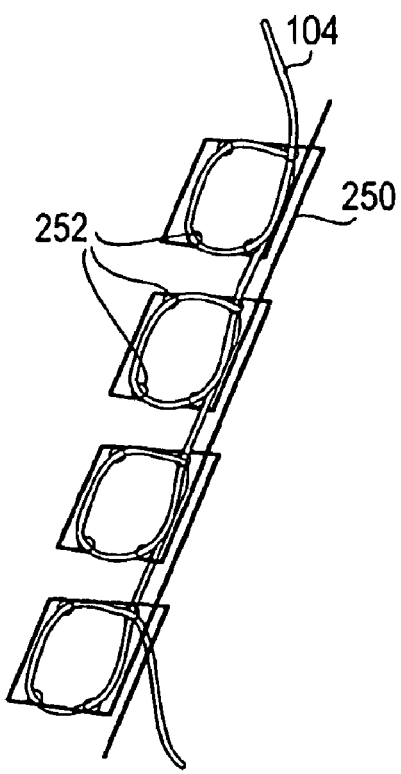
FIGS. 31-32 illustrate turns of a coil having shapes other than circular or oval.
Figure 32:
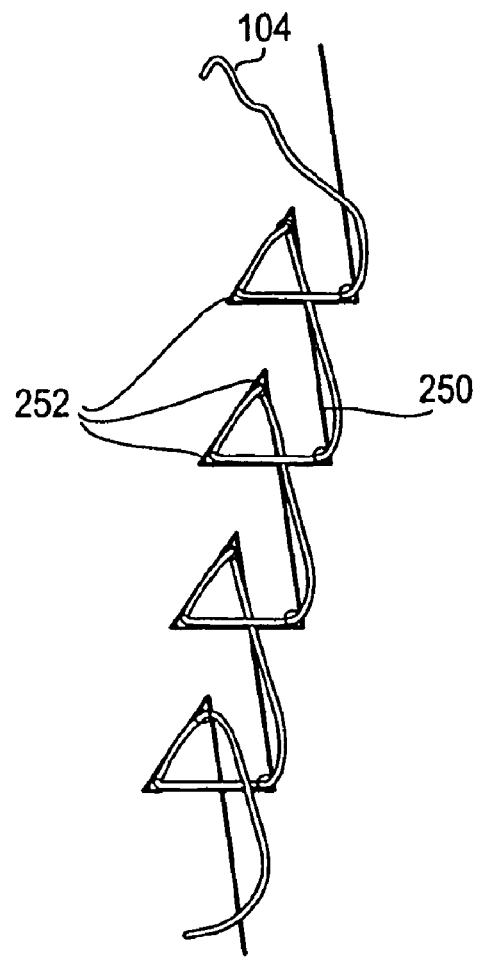

It may also be appreciated that the turns of the coil 250 may be shaped other than circular or oval. For example, as shown in FIG. 31, each turn of the coil 250 may be square or, as shown in FIG. 32, each turn of the coil 250 may be triangular. Suture retention loops 252 may be located along each turn, as shown, and a suture strand 104 is then threaded through the loops 252. Again, it may be appreciated that loops 252 may not be located along every turn of the coil and the suture strand 104 may be threaded through some or all of the loops in any configuration.

Figure 15C:
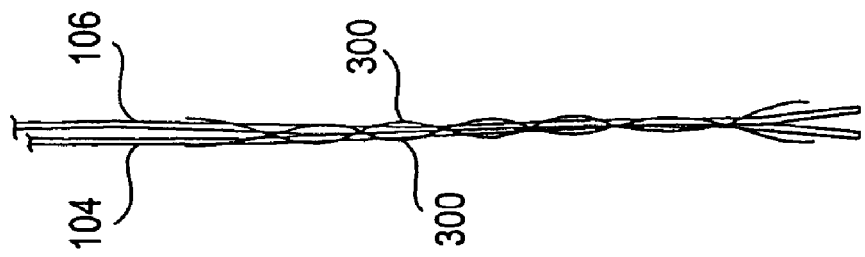
FIGS. 15A-15C illustrate a suture fastener comprising interlockable elements.
Figure 15B:
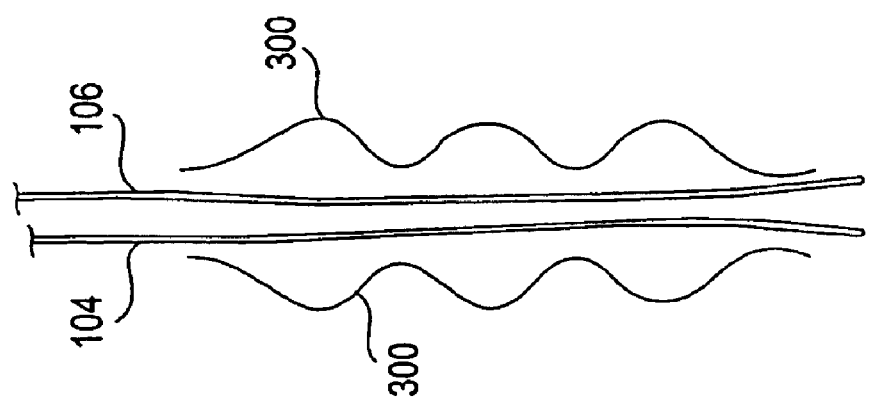
Figure 15A:
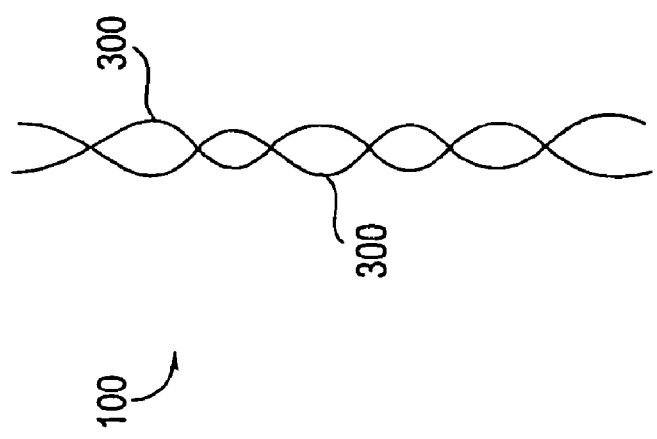

In other embodiments, the suture fastener 100 comprises two or more elements 300 which are interlockable, an example of which is illustrated in FIGS. 15A-15C. Referring to FIG. 15A, the fastener 100 is comprised of two elements 300 which are curved so that they interlock as shown when the element is in the relaxed shape-recovery position. Each element 300 may be comprised of an elongate wire, ribbon, rod, filament, shaft, braid, strand, cable, hypotube, weave, or mesh, to name a few. As shown in FIG. 15B, the elements 300 may be separated, straightened, held open or untwisted in the tensioned position so that suture strands 104, 106 may be placed within or between them. In this arrangement, the strands 104, 106 may be moved or adjusted relative to the elements 300 or each other. When the elements 300 return to the relaxed shape-recovery position, the elements 300 interlock around the strands, as shown in FIG. 15C, so that the suture strands 104, 106 are held in a fixed position relative to the element 300 and each other. Similarly, in another embodiment, the fastener 100 is comprised of one element which has a straight configuration in the tensioned position and a curved configuration in the relaxed shape-recovery position so that the curved configuration can hold suture strands 104, 106 in a fixed position.

Figure 16A:
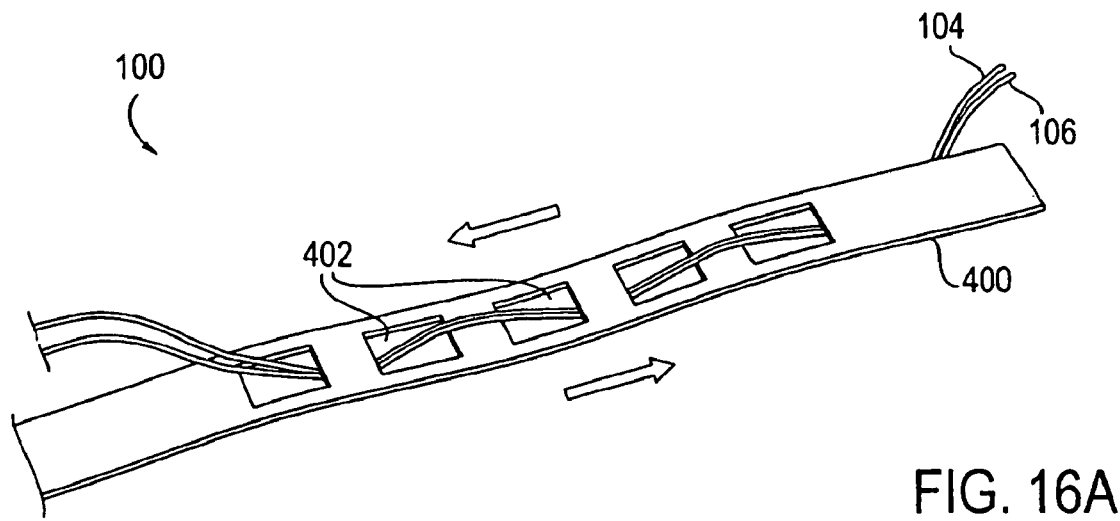
FIGS. 16A-16B illustrate a suture fastener comprising an element having a flat shape when in a tensioned position and a curved shape when in a relaxed shape-recovery position.
Figure 16B:
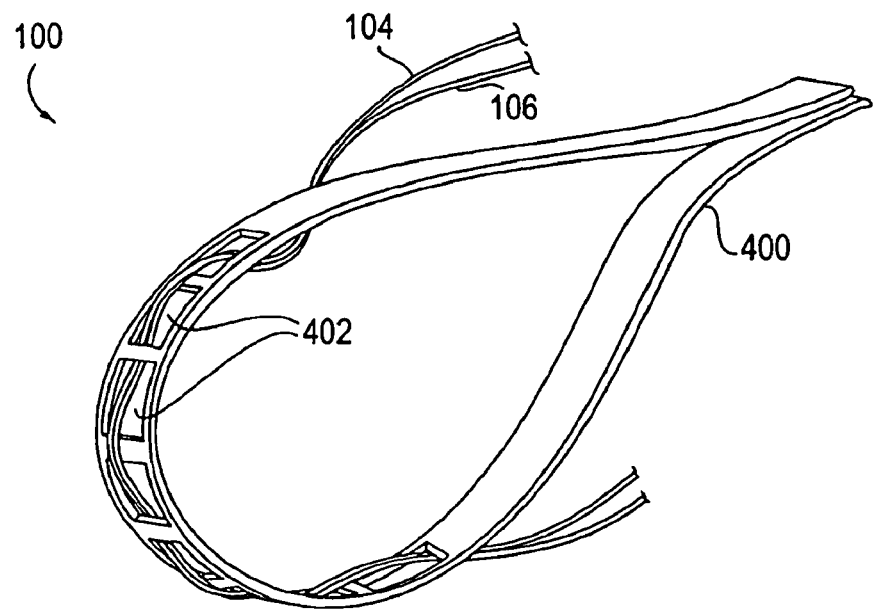

In additional embodiments, the suture fastener 100 comprises an element 400 which has a flat shape when in the tensioned position and a curved or bent shape when in the relaxed shape-recovery position, an example of which is illustrated in FIGS. 16A-16B. Referring to FIG. 16A, the element 400 is comprised of elongate wire, ribbon, rod, filament, shaft, mesh or woven sheet, to name a few, having two or more apertures 402 along its length. In a preferred embodiment, the element 400 comprises a ribbon having a width in the range of approximately 0.030 to 0.120 inches and a thickness in the range of approximately 0.002 to 0.010 inches. The suture strands 104, 106 are threaded through the apertures 402 in an alternating fashion as shown. Alternatively, the strands 104, 106 may be threaded in another arrangement which engages the strands 104, 106 with the element 400 yet allows the strands 104, 106 to slide relative to the element 400, as illustrated by arrows. When the element 400 forms the relaxed shape-recovery position, shown in FIG. 16B, the element 400 forms a curved or bent shape which prevents the strands 104, 106 from sliding relative to the element 400. Thus, the strands 104, 106 are fixed in place.

Figure 17A:
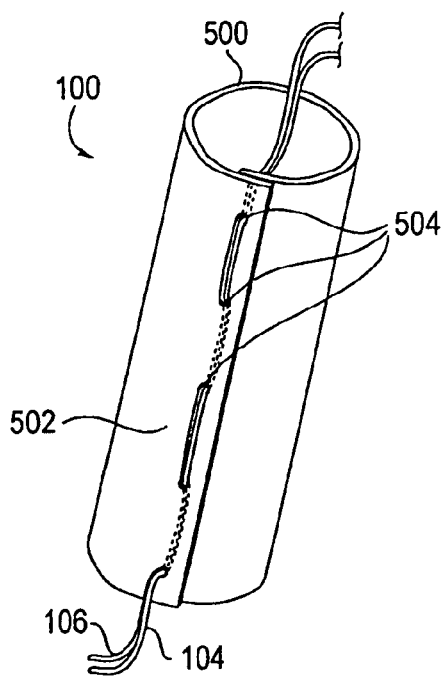
FIGS. 17A-17B illustrate a cylindrically shaped element having first and second portions with apertures for positioning suture strands.
Figure 17B:
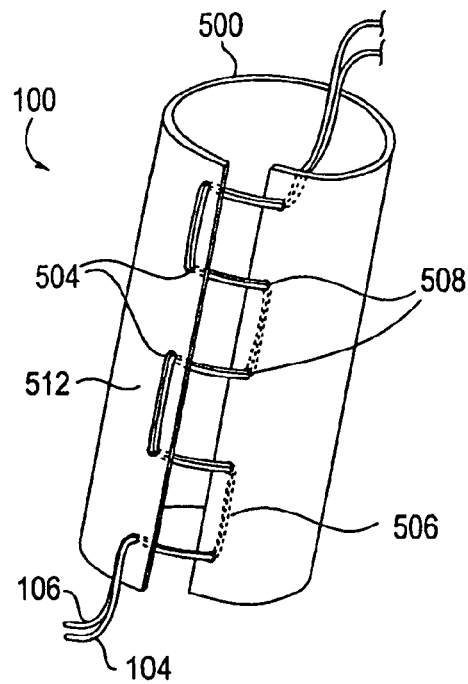
Figure 18A:
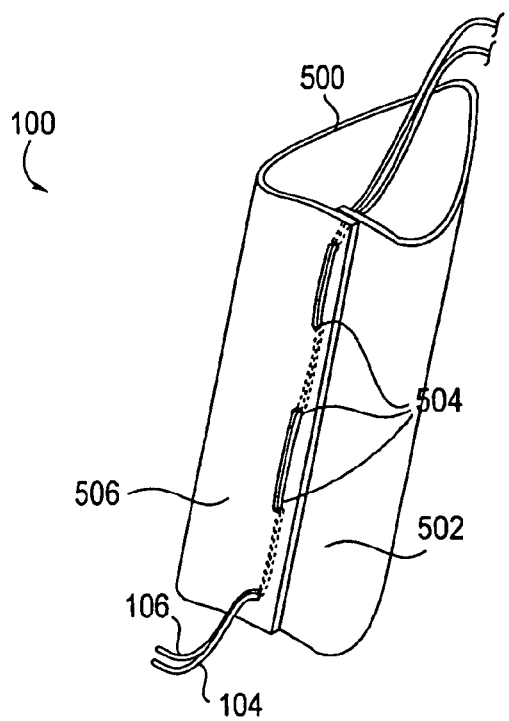
FIGS. 18A-18B illustrate a triangularly shaped element having first and second portions with apertures for positioning suture strands.
Figure 18B:
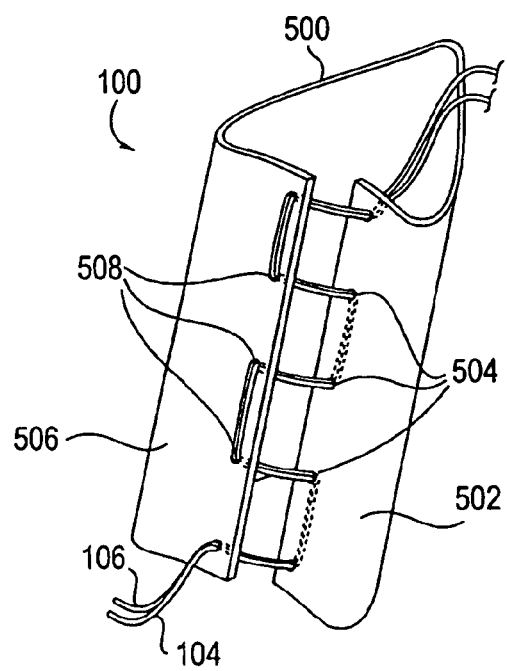

In still further embodiments, illustrated in FIGS. 17A-17B and FIGS. 18A-18B, the suture fastener 100 comprises an element 500 which has a first portion 502 having at least one first aperture 504 and a second portion 506 having at least one second aperture 508. Referring to FIG. 17A, the element 500 may have a cylindrical shape wherein the portions 502, 506 comprise end flaps as shown. By placing the element 500 in the tensioned position, the portions 502, 506 are overlapped so that at least one first aperture 504 is concentrically aligned with at least one second aperture 508. Suture strands 104, 106 threaded through the apertures 504, 508, as shown, may thus slide in relation to the element 500 for adjustment of the position of the element 500. When the element 500 is placed in the relaxed shape-recovery position, shown in FIG. 17B, the at least one first aperture 504 is then misaligned with the at least one second aperture 508. In this configuration, it is much more difficult for the suture strands 104, 106 to slide relative to the element 500 so the strands 104, 106 are essentially fixed in place. Similarly, as shown in FIGS. 18A-18B, the element 500 may have a triangular shape wherein the portions 502, 506 comprise end flaps as shown. In this embodiment, the element 500 functions as in FIGS. 17A-17B respectively.

Figure 33A:
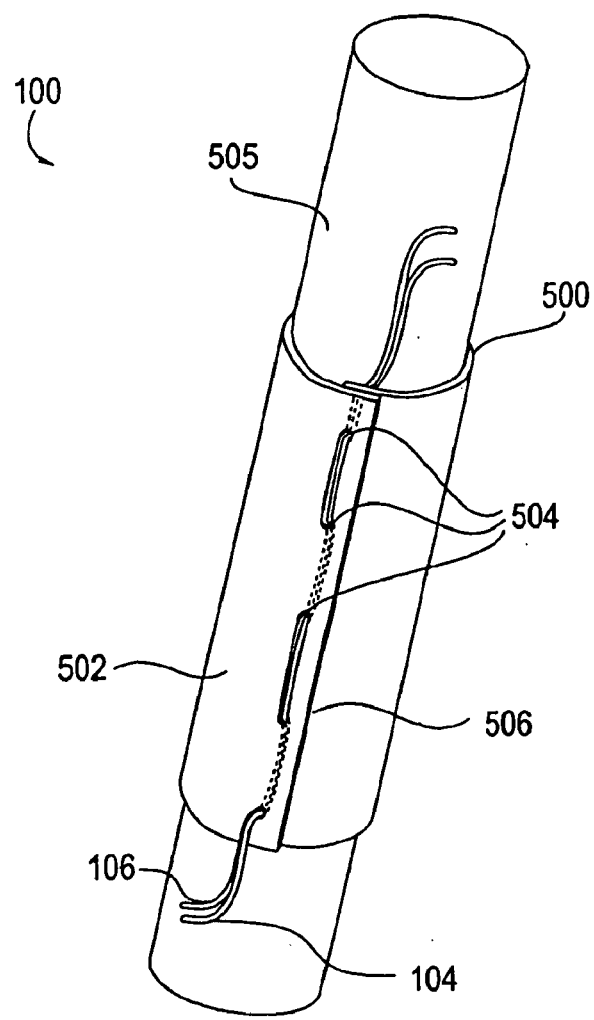
FIG. 33A illustrates an embodiment of an element in a tensioned position having portions which are overlapped so that at least one aperature is concentrically aligned with another aperture.
Figure 33B:
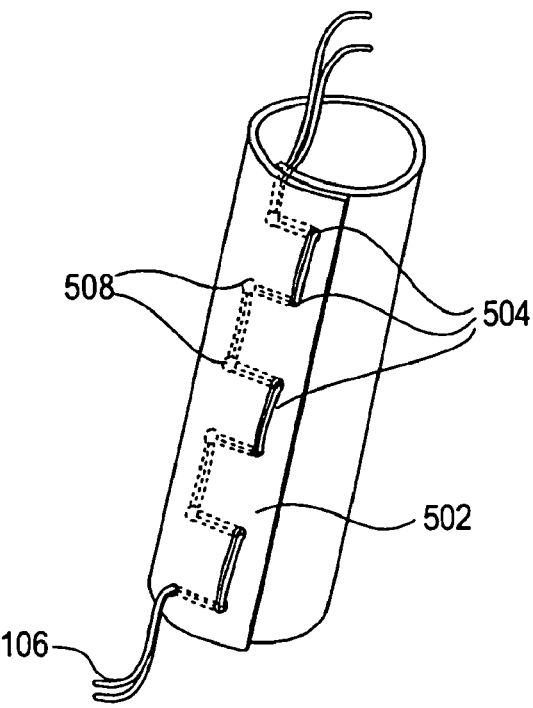
FIG. 33B illustrates the embodiment of FIG. 33A in a relaxed position wherein the apertures are misaligned.

In another embodiment, illustrated in FIGS. 33A-33B, the element 500 again has a first portion 502 having at least one first aperture 504 and a second portion 506 having at least one second aperture 508. Referring to FIG. 33A, the element 500 may have a cylindrical shape wherein the portions 502, 506 comprise end flaps as shown. By placing the element 500 in the tensioned position, the portions 502, 506 are overlapped so that at least one first aperture 504 is concentrically aligned with at least one second aperture 508. The element may be held in the tensioned position by the insertion of a mandrel 505, as shown, or by any other suitable means. Suture strands 104, 106 threaded through the apertures 504, 508, as shown, may thus slide in relation to the element 500 for adjustment of the position of the element 500. When the mandrel 505 is removed element 500 is placed in the relaxed shape-recovery position, shown in FIG. 33B, the at least one first aperture 504 is then misaligned with the at least one second aperture 508 by inward recoiling of the element 500. In this configuration, it is much more difficult for the suture strands 104, 106 to slide relative to the element 500 so the strands 104, 106 are essentially fixed in place.

Figure 19:
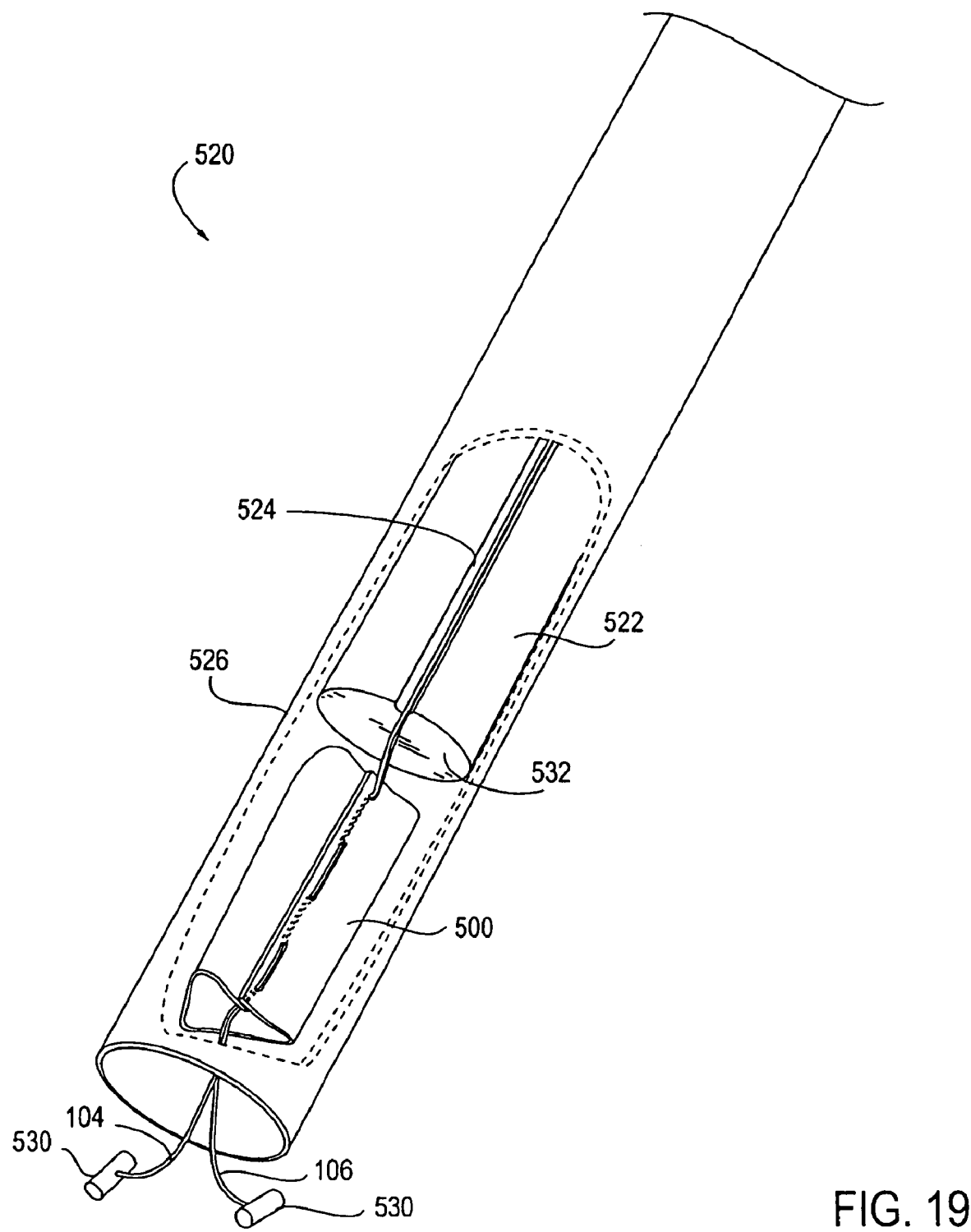
FIG. 19 illustrates an embodiment of a delivery catheter for delivery and deployment of a fastening element.

FIG. 19 illustrates an embodiment of a delivery catheter 520 for delivery and deployment of the element 500. Here, the delivery catheter 520 comprises a push rod 522, having a slot 524 therethrough, surrounded by an outer tube 526. The element 500 is loaded, in the compressed or tensioned position, within the outer tube 526 distal to the push rod 522. Suture strands 104, 106 are threaded through the element 500, as previously described in relation to FIGS. 17A-17B and FIGS. 18A-18B, and through the slot 524 in the push rod 522. Once the sutures 104, 106 are positioned in the tissue (not shown), such as through valve leaflets wherein anchors 530 at the ends of the sutures 104, 106 rest against the underside of the leaflets, the element 500 may be positioned at a desired location along the suture strands 104, 106. Once in this position, the element 500 is deployed from the catheter 520 by pushing the element 500 out of the outer tube 526 with the push rod 522. A cutting mechanism 532 may also be integral with the push rod 522 to cut the suture strands 104, 106 and leave the element 500 in place.

Figure 20A:
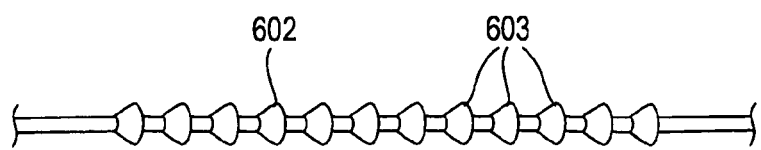
FIGS. 20A-20B depict textured suture strands.
Figure 20B:
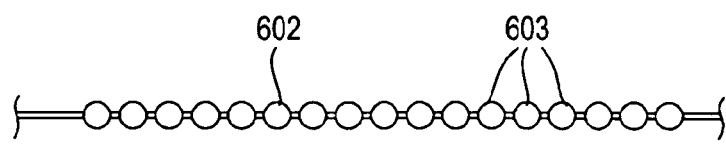

In additional embodiments, the suture fastener 100 comprises a ratcheting mechanism 600 for securing a textured suture strand 602. Typically, such suture strands 602 are comprised of a fiber, thread, filament, wire or cord and may be textured by any means to provide a surface having protuberances 603 for securing with the ratcheting mechanism 600. Protuberances may include knots, beads, balls, ribs and spokes. For example, an embodiment of a suture strand 602 having a ribbed texture is shown in FIG. 20A, and an embodiment having a beaded texture is shown in FIG. 20B. The suture strand 602 or at least one protuberance 603 may be comprised of any suitable material, such as stainless steel, metal, polymer, silicone, latex, epoxy, cotton, nylon, polyester and Teflon, to name a few. For example, the suture strands 602 may be formed by extruding the desired texture with a rigid polymer over a stainless steel core wire. Alternatively, knots may be tied in increments along a flexible suture strand to provide a suitable texture.

Figure 21A:
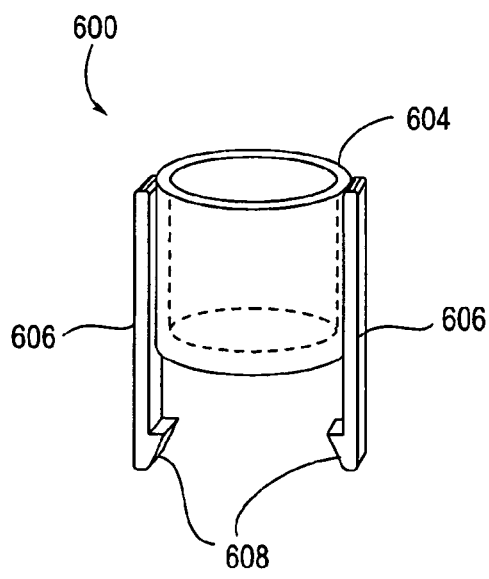
FIGS. 21A-21B illustrate embodiments of a ratchet for use with textured suture strands.
Figure 21B:
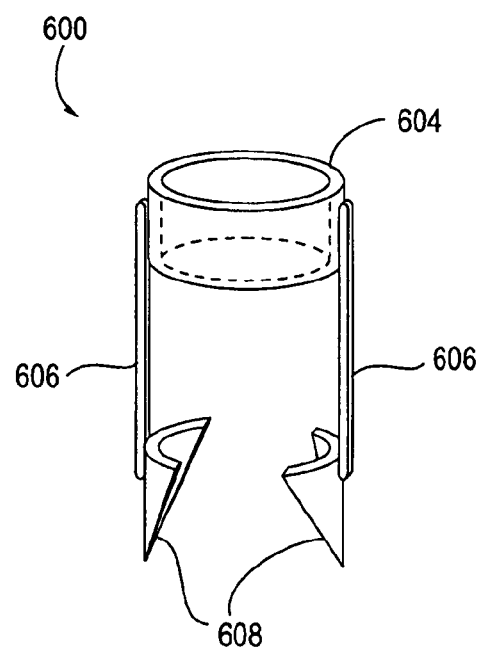

FIGS. 21A-21B illustrate embodiments of the ratcheting mechanism 600 for use with the textured suture strand 602. As shown in FIGS. 21A-21B, the ratcheting mechanism 600 may include a cylindrical tube 604 having flexible arms 606 thereattached. Stoppers 608 are attached near the distal end of the arms 606 as shown. The stoppers 608 are used to nestle between the protuberances 603 of the suture strand 602 and hold the strand 602 in place. For example, the ratcheting mechanism 600 may be adapted to hold the suture strand 602 at a first location and then release the strand 602 and hold the strand 602 at a second location upon adjustment, wherein the first and second locations are a predetermined distance apart. Referring to FIG. 22, the suture fastener 100 may further comprise a housing 610 having a flange 612 for tissue contact wherein the ratcheting mechanism 600 is housed within. The fastener 100 may be mounted on the distal end 622 of a delivery catheter 520 for placement in a desired location along a suture strand 602. As shown in FIG. 23, valve leaflets LF may be fixed together by a suture strand 602. Suture fasteners 100 may be positioned along the suture strand 602, as shown, so that the flanges 612 contact the surfaces of the leaflets LF. The position of the fasteners 100 may be adjusted by advancing the suture strand 602 through the ratcheting mechanism 600. The suture strand 602 is then held in place by action of the stoppers 608 in the protuberances 603 as described above. Similarly, as shown in FIGS. 24A-24B, one suture fastener 100 may be used to fix a pair of leaflets together. In FIG. 24A, the suture strand 602 is passed through each of the leaflets LF wherein one end of the strand 602 forms a loop 624 through which the other free end 626 of the strand 602 is passed. The fastener 100 is then positioned along this free end 626 and adjusted and/or secured as described in relation to FIG. 23. In FIG. 24B, the suture strand 602 is passed through each of the leaflets LF so that both free ends 626 are on one side of the leaflets LF. The fastener 100 is then positioned along both free ends 626, as shown, and adjusted and/or secured as described in relation to FIG. 23.

Figure 25:
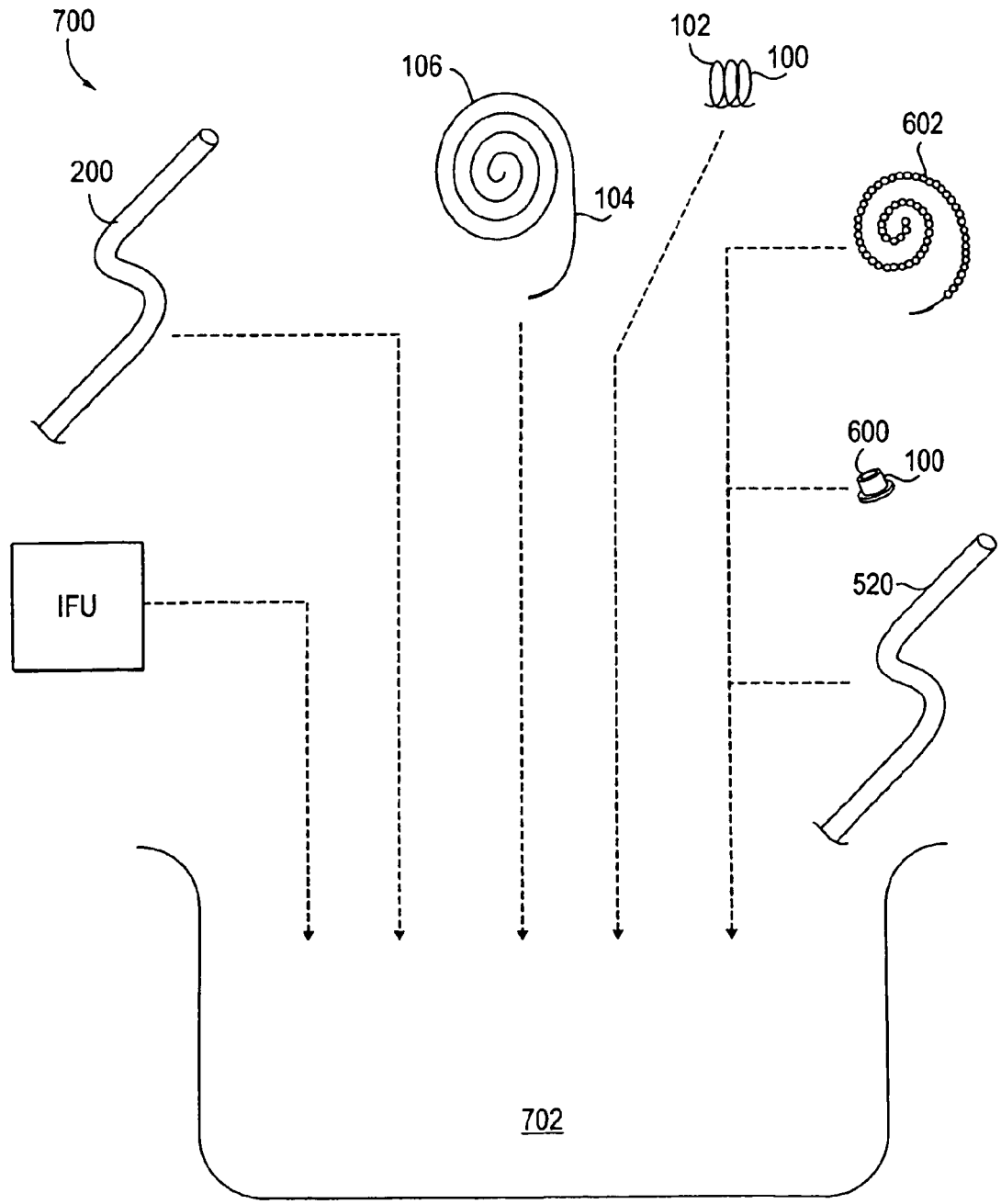
FIG. 25 illustrates a kit in accordance with the present invention.

Referring now to FIG. 25, kits 700 according to the present invention comprise at least a suture fastener 100 and instructions for use IFU. Such kits may include more than one suture fastener which may include different features, such as element 102 or ratcheting mechanism 600. Optionally, the kits may further include one or more of any of the other system components described above, such as a loading tool 200, a suture strands 104, 106, a textured suture strand 602, and/or a delivery catheter 520. In addition, other items may be included related to the medical procedure, such as catheters, guidewires, introducers, dilators, and needles, to name a few. The instructions for use IFU will set forth any of the methods as described above, and all kit components will usually be packaged together in a pouch 702 or other conventional medical device packaging. Usually, those kit components, such as suture fasteners 100, which will be used in performing the procedure on the patient will be sterilized and maintained within the kit. Optionally, separate pouches, bags, trays or other packaging may be provided within a larger package, where the smaller packs may be opened separately to separately maintain the components in a sterile fashion.

Although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. A suture fastening system for adjustably holding suture, said system comprising:
   one or more suture strands; and
   a tubular fastening element of unitary construction having a hollow central channel, the fastening element comprised of a shape memory alloy or a spring temper steel, said fastening element comprising at least one pair of discrete through holes in a sidewall thereof, at least one of said one or more suture strands at least partially received through said at least one pair of discrete though holes, wherein the fastening element has a tensioned shape-recovery position in which the discrete through holes of said at least one pair of discrete through holes are concentrically aligned to allow for sliding of the fastening element relative to the suture strands and a relaxed shape-recovery position in which the discrete through holes of said at least one pair of discrete through holes are misaligned for holding the strands in a fixed position relative to the element or to each other, and wherein the fastener is adjustable between the tensioned shape-recovery position and the relaxed shape-recovery position to allow repositioning of the fastener to a new desired location along the suture strands after holding the strands in a fixed position, and wherein the at least one pair of discrete through holes comprises at least one first discrete through hole and at least one second discrete through hole, the at least one suture strand passing directly from the at least one first discrete through hole to the at least one second discrete through hole, and wherein the at least one pair of discrete through holes are bounded on all sides in both the tensioned position and the relaxed position,
   wherein the fastening element holds the suture strands along a tortuous path in the relaxed shape-recovery position,
   wherein the tortuous path has a circumferentially offset form.

2. A system as in claim 1, wherein the fastening element holds the suture strands along a substantially straight path in the tensioned shape-recovery position.

3. A system as in claim 1, wherein the at least one pair of discrete through holes comprises at least two pair of discrete through holes disposed along the length of the fastening element.

4. A system as in claim 1, wherein the fastening element has a first edge having the at least one first discrete through hole adjacent thereto and a second edge having the at least one second discrete through hole adjacent thereto.

5. A system as in claim 4, wherein at least part of the first edge overlaps at least part of the second edge when the fastening element is in the tensioned shape-recovery position.

6. A system as in claim 1, wherein the fastening element is transitionable from the tensioned shape-recovery position to the relaxed position by release of a force on the fastening element.

7. A system as in claim 1, wherein the fastening element is transitionable from the tensioned shape-recovery position to the relaxed position by a change in temperature of the fastening element.

8. A system as in claim 1, wherein the tubular fastening element has a longitudinal axis, and wherein the fastening element has first and second edges substantially parallel with the longitudinal axis, the first edge having the at least one first discrete through hole adjacent thereto and the second edge having the at least one second discrete through hole adjacent thereto, wherein the at least one first discrete through hole is concentrically aligned with the at least one second discrete through hole when the fastening element is in the tensioned shape-recovery position, and the at least one first discrete through hole is misaligned with the at least one second discrete through hole when the element is in the relaxed shape-recovery position.

9. A suture fastening system for adjustably holding suture, said system comprising:
   one or more suture strands; and
   a tubular fastening element of unitary construction having a hollow central channel, said fastening element including at least one pair of discrete through holes through a sidewall of the fastening element, each of said discrete through holes being bounded on all sides, at least one of said one or more suture strands at least partially received through said at least one pair of discrete through holes, wherein the fastening element has a tensioned shape-recovery position in which the discrete through holes of said at least one pair of discrete through holes are concentrically aligned to allow for sliding of the fastening element relative to the suture strands and a relaxed shape-recovery position in which the discrete through holes of said at least one pair of discrete through holes are misaligned for holding the strands in a fixed position relative to the element or to each other, and wherein the fastener is adjustable between the tensioned shape-recovery position and the relaxed shape-recovery position to allow repositioning of the fastener to a new desired location along the suture strands after holding the strands in a fixed position, and wherein the at least one pair of discrete through holes comprises a first discrete through hole and a second discrete through hole, the at least one suture strand passing directly from the first discrete through hole to the second discrete through hole, and wherein the at least one pair of discrete through holes are bounded on all sides in both the tensioned position and the relaxed position, wherein the fastening element holds the suture strands along a tortuous path in the relaxed shape-recovery position, wherein the tortuous path has a circumferentially offset form.

* * * * *